(12) United States Patent
Hyde et al.

(10) Patent No.: US 8,712,794 B2
(45) Date of Patent: *Apr. 29, 2014

(54) METHODS AND SYSTEMS FOR PRESENTING AN INHALATION EXPERIENCE

(75) Inventors: Roderick A. Hyde, Redmond, WA (US); Robert Langer, Newton, MA (US); Eric C. Leuthardt, St. Louis, MO (US); Robert W. Lord, Seattle, WA (US); Elizabeth A. Sweeney, Seattle, WA (US); Clarence T. Tegreene, Bellevue, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 649 days.

This patent is subject to a terminal disclaimer.

(21) Appl. No.: 12/387,057

(22) Filed: Apr. 27, 2009

(65) Prior Publication Data

US 2010/0164729 A1    Jul. 1, 2010

Related U.S. Application Data

(63) Continuation-in-part of application No. 12/317,934, filed on Dec. 30, 2008, and a continuation-in-part of application No. 12/319,143, filed on Dec. 31, 2008, and a continuation-in-part of application No. 12/378,284, filed on Feb. 12, 2009, and a continuation-in-part of application No. 12/378,485, filed on Feb. 13, 2009, and a continuation-in-part of application No. 12/380,013, filed on Feb. 20, 2009, and a continuation-in-part of application No. 12/380,108, filed on Feb. 23, 2009, and a continuation-in-part of application No. 12/380,587, filed on Feb. 27, 2009, and a continuation-in-part of application No. 12/380,679, filed on Mar. 2, 2009, and a continuation-in-part of application No. 12/383,509, filed on Mar. 25, 2009, and a continuation-in-part of application No. 12/383,819, filed on Mar. 26, 2009, and a continuation-in-part of application No. 12/384,104, filed on Mar. 31, 2009, and a continuation-in-part of application No. 12/384,203, filed on Apr. 1, 2009, and a continuation-in-part of application No. 12/386,574, filed on Apr. 20, 2009, and a continuation-in-part of application No. 12/386,669, filed on Apr. 21, 2009.

(51) Int. Cl.
*G06Q 10/00* (2012.01)
*G06F 19/00* (2011.01)
*A61M 11/00* (2006.01)

(52) U.S. Cl.
USPC .............................. 705/2; 702/19; 128/200.15

(58) Field of Classification Search
USPC ............................................................ 705/2
See application file for complete search history.

(56) References Cited

U.S. PATENT DOCUMENTS 3,946,726 A    3/1976  Pikul
(Continued)

FOREIGN PATENT DOCUMENTS

EP    0328145    8/1989

OTHER PUBLICATIONS

Dog Health: Asthma, http://www.animalhospitals-usa.com/dogs/asthma.html, 2009, Publisher: Harper Collins.

(Continued)

*Primary Examiner* — Hiep V Nguyen

(57) ABSTRACT

Methods, computer program products, and systems are described that include accepting an indication of an individual's compliance with an artificial sensory experience and presenting an indication of an inhalation device-dispensed bioactive agent at least partially based on the indication of the individual's compliance with the artificial sensory experience.

40 Claims, 35 Drawing Sheets

(56) References Cited

U.S. PATENT DOCUMENTS

| | | | |
|---|---|---|---|
| 4,652,261 A | 3/1987 | Mech et al. |
| 4,784,162 A | 11/1988 | Ricks et al. |
| 4,974,729 A | 12/1990 | Steinnagel |
| 5,071,704 A | 12/1991 | Fischel-Ghodsian |
| 5,455,043 A | 10/1995 | Fischel-Ghodsian |
| 5,458,853 A | 10/1995 | Porter et al. |
| 5,487,378 A | 1/1996 | Robertson et al. |
| 5,546,943 A | 8/1996 | Gould |
| 5,610,674 A | 3/1997 | Martin |
| 5,709,863 A | 1/1998 | Pageat |
| 5,725,472 A * | 3/1998 | Weathers ................. 600/21 |
| 5,822,726 A | 10/1998 | Taylor et al. |
| 5,842,467 A | 12/1998 | Greco |
| 5,954,641 A | 9/1999 | Kehr et al. |
| 6,026,807 A | 2/2000 | Puderbaugh et al. |
| 6,067,523 A | 5/2000 | Bair et al. |
| 6,168,562 B1 | 1/2001 | Miller et al. |
| 6,223,744 B1 | 5/2001 | Garon |
| 6,280,383 B1 | 8/2001 | Damadian |
| 6,314,384 B1 | 11/2001 | Goetz |
| 6,315,719 B1 | 11/2001 | Rode et al. |
| 6,338,338 B1 | 1/2002 | Brace |
| 6,411,905 B1 | 6/2002 | Guoliang et al. |
| 6,425,764 B1 | 7/2002 | Lamson |
| 6,443,153 B1 | 9/2002 | Viljanen et al. |
| 6,491,643 B2 | 12/2002 | Katzman et al. |
| 6,500,862 B1 | 12/2002 | Zanello |
| 6,513,523 B1 | 2/2003 | Izuchukwu et al. |
| 6,585,519 B1 | 7/2003 | Jenkins et al. |
| 6,609,068 B2 | 8/2003 | Cranley et al. |
| 6,647,358 B2 | 11/2003 | Grass et al. |
| 6,684,880 B2 * | 2/2004 | Trueba ................. 128/200.16 |
| 6,780,171 B2 | 8/2004 | Gabel et al. |
| 6,783,753 B2 | 8/2004 | Rabinowitz et al. |
| 6,860,239 B1 | 3/2005 | Begun |
| 6,889,687 B1 | 5/2005 | Olsson |
| 6,978,212 B1 | 12/2005 | Sunshine |
| 6,981,502 B2 | 1/2006 | McCormick et al. |
| 7,044,911 B2 | 5/2006 | Drinan et al. |
| 7,155,680 B2 | 12/2006 | Akazawa et al. |
| 7,198,044 B2 | 4/2007 | Trueba |
| 7,353,065 B2 | 4/2008 | Morrell |
| 7,373,377 B2 | 5/2008 | Altieri |
| 7,383,837 B2 | 6/2008 | Robertson et al. |
| 7,427,417 B2 | 9/2008 | Jendrucko et al. |
| 7,447,541 B2 | 11/2008 | Huiku et al. |
| 7,720,696 B1 | 5/2010 | Berger et al. |
| 8,068,983 B2 | 11/2011 | Vian et al. |
| 2001/0006939 A1 | 7/2001 | Niven et al. |
| 2001/0034023 A1 | 10/2001 | Stanton, Jr. et al. |
| 2002/0084996 A1 | 7/2002 | Temkin et al. |
| 2003/0032638 A1 | 2/2003 | Kim et al. |
| 2003/0036683 A1 | 2/2003 | Kehr et al. |
| 2003/0114475 A1 | 6/2003 | Fox et al. |
| 2004/0107961 A1 | 6/2004 | Trueba |
| 2004/0116784 A1 * | 6/2004 | Gavish ................. 600/300 |
| 2004/0254501 A1 | 12/2004 | Mault |
| 2005/0054942 A1 | 3/2005 | Melker et al. |
| 2005/0115561 A1 | 6/2005 | Stahmann et al. |
| 2005/0220843 A1 | 10/2005 | DeWitt et al. |
| 2006/0031099 A1 * | 2/2006 | Vitello et al. ................. 705/2 |
| 2006/0058694 A1 | 3/2006 | Clark et al. |
| 2006/0207596 A1 | 9/2006 | Lane |
| 2007/0068514 A1 | 3/2007 | Giroux |
| 2007/0068515 A1 | 3/2007 | Churchill |
| 2007/0112624 A1 | 5/2007 | Jung et al. |
| 2007/0123783 A1 | 5/2007 | Chang |
| 2008/0014566 A1 * | 1/2008 | Chapman et al. ............. 434/262 |
| 2008/0038701 A1 | 2/2008 | Booth et al. |
| 2008/0087279 A1 | 4/2008 | Tieck et al. |
| 2008/0142010 A1 | 6/2008 | Weaver et al. |
| 2008/0172044 A1 | 7/2008 | Shelton |
| 2008/0209289 A1 | 8/2008 | Farnsworth et al. |
| 2008/0230057 A1 | 9/2008 | Sutherland |
| 2008/0294012 A1 | 11/2008 | Kurtz et al. |
| 2008/0318913 A1 | 12/2008 | Fox et al. |
| 2009/0171259 A1 | 7/2009 | Soerensen et al. |
| 2009/0223249 A1 | 9/2009 | Julkowski et al. |
| 2009/0306741 A1 | 12/2009 | Hogle et al. |
| 2011/0226242 A1 | 9/2011 | Von Hollen et al. |

OTHER PUBLICATIONS

Karen Vail, Chemical and Nonchemical Management of Fleas, 1999, Publisher: facilities.lipscomb.edu/media.asp?SID=145&UKEY=7743, Published in: US.

Julian R. Yates III, Ctenocephalides felis (Bouche), http://www.extento.hawaii.edu/kbase/urban/site/catflea.htm, Published in: US.

Mehlhorn, et al., Effects of Imidacloprid on Adult and Larval Stages of the Flea Ctenocephalides Felis After In Vivo and In Vitro Applicat, Parasitology Research, 1999, pp. 625-637, vol. 85, No. 8-9, Published in: US.

Susan Little, Feline Asthma, The Winn Feline Foundation, 2003, Publisher: http://www.winnfelinehealth.org/health/asthma.html, Published in: US.

Placerville Veterinary Clinic, Flea Control, www://placervillevet.com/flea_control.htm, 1995-2008, Published in: US.

Cranshaw, et al., Fleas and Plague, http://www.ext.colostate.edu/pubs/insect/05600.html, 2008, Published in: US.

Jeff Feinman, VMD,CVH, Fleas and Ticks, http://www.homevet.com/petcare/fleas.html, 1996-1997, Published in: US.

Omar S. Usmani, et al., Glucocorticoid Receptor Nuclear Translocation in Airway Cells After Inhaled Combination Therapy, American Journal of Respiratory and Critical Care Medicine, Apr. 28, 2005, pp. 704-712, vol. 172, Published in: US; printed from http://ajrccm.atsjournals.org/cgi/content/abstract/172/6/704 on Apr. 2, 2009.

J.B. Siddall, Insect Growth Regulators and Insect Control: A Critical Appraisal, Environmental Health Perspectives, Apr. 1976, pp. 119-126, vol. 14, Published in: US.

Label Instructions Tightened on Flea & Tick Control Products for Pets, http://www.epa.gov/pesticides/factsheets/hartzq_a.htm, Nov. 2002, Publisher: Environmental Protection Agency, Published in: US.

T. Roy Fukuto, Mechanism of Action of Organophosphorus and Carbamate Insecticides, Environmental Health Perspectives, Jul. 1990, pp. 245-254, vol. 87, Published in: US.

M. Tomizawa, et al., Neonicotinoid Insecticide Toxicology: Mechanisms of Selective Action, Annual Review of Pharmacology and Toxicology, Feb. 2005, pp. 247-268, vol. 45.

C.J. Harland, et al., Remote Detection of Human Electroencephalograms Using Ultrahigh Input Impedance Electric Potential Sensors, Applied Physics Letters, Oct. 21, 2002, pp. 3284-3286, vol. 81, No. 17, Publisher: American Institute of Physics.

Mencke, et al., Therapy and Prevention of Parasitic Insects in Veterinary Medicine Using Imidacloprid, Current Topics in Medicinal Chemistry, Jul. 2002, vol. 2, No. 7.

Hovda, et al., Toxicology of Newer Pesticides for Use in Dogs and Cats, Vet Clin North Am Small Anim. Pract., Mar. 2002, pp. 455-567, vol. 32, No. 2.

U.S. Appl. No. 12/387,151, Hyde et al.
U.S. Appl. No. 12/387,321, Hyde et al.
U.S. Appl. No. 12/387,472, Hyde et al.

"Fear of Flying"; The Virtual Reality Medical Center (VRMC); Bearing a date of Jan. 1, 2007, p. 1; located at: http://www.vrphobia.com/therapy.htm.

* cited by examiner

600

610
accepting an indication of a bioactive agent-dispensing inhalation device

620
presenting an indication of an artificial sensory experience at least partially based on accepting an indication of a bioactive agent-dispensing inhalation device

Start

610
accepting an indication of a bioactive agent-dispensing inhalation device

| 702 accepting an indication of a bioactive agent-dispensing inhalation device configured to interface with a computing device | 706 accepting an indication of a bioactive agent-dispensing inhalation collar | 708 accepting an indication of a bioactive agent-dispensing virtual-reality headset |
|---|---|---|
| 704 accepting an indication of a bioactive agent-dispensing inhalation device configured to interface wirelessly with a computing device | | |

620
presenting an indication of an artificial sensory experience at least partially based on accepting an indication of a bioactive agent-dispensing inhalation device Finish

FIG. 7

```
┌─────────┐
│  Start  │
└────┬────┘
     │                                    600 ↙
┌────┴──────────────────────────────────────────────────────┐
│ 610                                                        │
│ accepting an indication of a bioactive agent-dispensing    │
│ inhalation device                                          │
│ ┌─────────────────┐ ┌───────────────────────────────────┐ │
│ │ 902             │ │ 904                               │ │
│ │ accepting    an │ │ accepting an indication of a recreational │
│ │ indication of an│ │ bioactive agent-dispensing inhalation device │
│ │ unregulated bioactive│ ├───────────────────────────────┤ │
│ │ agent-dispensing│ │ 906                               │ │
│ │ inhalation device│ │ accepting an indication of at least one │
│ │                 │ │ artificial smoke or an aroma compound │
│ └─────────────────┘ └───────────────────────────────────┘ │
└────────────────────────────┬──────────────────────────────┘
                             │
┌────────────────────────────┴──────────────────────────────┐
│ 620                                                        │
│ presenting an indication of an artificial sensory experience at least partially │
│ based on accepting an indication of a bioactive agent-dispensing inhalation │
│ device                                                     │
└────────────────────────────┬──────────────────────────────┘
                        ┌────┴────┐
                        │ Finish  │
                        └─────────┘
```

Start

610
accepting an indication of a bioactive agent-dispensing inhalation device 620
presenting an indication of an artificial sensory experience at least partially based on accepting an indication of a bioactive agent-dispensing inhalation device 1002 presenting an indication of a prescribed artificial sensory experience

| 1102 presenting an indication of at least one time period of an expected change in bioactive agent effectiveness | 1104 presenting an indication of at least one time period of an expected change in bioactive agent blood concentration | 1106 recommending an artificial sensory experience administration schedule |

Finish

Start

610
accepting an indication of a bioactive agent-dispensing inhalation device 620
presenting an indication of an artificial sensory experience at least partially based on accepting an indication of a bioactive agent-dispensing inhalation device

| 1302 presenting an indication of an artificial sensory experience at least partly based on a medical reference tool | 1304 presenting the indication to at least one output device |
|---|---|
| | 1306 presenting the indication to at least one user interface | 1308 presenting the indication to at least one mobile device |

Finish

Start 2210
accepting an indication of an individual's compliance with an artificial sensory experience 2220
presenting an indication of an inhalation device-dispensed bioactive agent at least partially based on the indication of the individual's compliance with the artificial sensory experience Finish

FIG. 22

```
                          Start
                                        ← 2200

2210
accepting an indication of an individual's compliance with an
artificial sensory experience
  ┌─ ─ ─ ─ ─ ─ ─ ─ ─ ─ ─ ┐  ┌─ ─ ─ ─ ─ ─ ─ ─ ─ ─ ─ ┐
  │ 2402                 │  │ 2404                 │
  │ accepting a report of the │ accepting a report of the │
  │ individual's compliance   │ individual's compliance   │
  │ from a health care        │ from an artificial sensory │
  │ provider                  │ experience provider        │
  │                      │  │                      │
  └─ ─ ─ ─ ─ ─ ─ ─ ─ ─ ─ ┘  └─ ─ ─ ─ ─ ─ ─ ─ ─ ─ ─ ┘

2220
presenting an indication of an inhalation device-dispensed
bioactive agent at least partially based on the indication of the
individual's compliance with the artificial sensory experience Finish
```

FIG. 24

```
                          ┌───────┐
                          │ Start │         ← 2200
                          └───┬───┘
                              │
┌─────────────────────────────┴──────────────────────────────────┐
│ 2210                                                            │
│ accepting an indication of an individual's compliance with an   │
│ artificial sensory experience                                   │
│  ┌─────────────────────────────────────────┐  ┌──────────────┐  │
│  │ 2502                                    │  │ 2508         │  │
│  │ accepting an indication of artificial   │  │ accepting    │  │
│  │ sensory experience usage by the         │  │ an           │  │
│  │ individual                              │  │ indication   │  │
│  │  ┌──────────────────────────────────┐   │  │ of           │  │
│  │  │ 2504                             │   │  │ interactive  │  │
│  │  │ accepting an indication of       │   │  │ device       │  │
│  │  │ computer usage                   │   │  │ usage        │  │
│  │  │  ┌─────────────────────────┐     │   │  │              │  │
│  │  │  │ 2506                    │     │   │  │              │  │
│  │  │  │ accepting an indication │     │   │  │              │  │
│  │  │  │ of at least one of      │     │   │  │              │  │
│  │  │  │ virtual world usage or  │     │   │  │              │  │
│  │  │  │ a computer activity log │     │   │  │              │  │
│  │  │  └─────────────────────────┘     │   │  │              │  │
│  │  └──────────────────────────────────┘   │  │              │  │
│  └─────────────────────────────────────────┘  └──────────────┘  │
└─────────────────────────────┬──────────────────────────────────┘
                              │
┌─────────────────────────────┴──────────────────────────────────┐
│ 2220                                                            │
│ presenting an indication of an inhalation device-dispensed      │
│ bioactive agent at least partially based on the indication of   │
│ the individual's compliance with the artificial sensory         │
│ experience                                                      │
└─────────────────────────────┬──────────────────────────────────┘
                              │
                          ┌───┴────┐
                          │ Finish │
                          └────────┘
```

FIG. 25

```
                              Start
                                │
                                ▼
2210
accepting an indication of an individual's compliance with an
artificial sensory experience ┌─────────────────────────────────────────────────────────┐
    │ 2702                                                    │
    │ accepting an indication of a physiological measurement  │
    │  ┌──────────────────┐ ┌──────────────┐ ┌──────────────┐ │
    │  │ 2704             │ │ 2706         │ │ 2708         │ │
    │  │ accepting an     │ │ continuously │ │ accepting an │ │
    │  │ indication of at │ │ monitoring a │ │ indication of│ │
    │  │ least one of a   │ │ parameter of │ │ a current    │ │
    │  │ respiratory rate,│ │ a            │ │ parameter    │ │
    │  │ body weight,     │ │ physiological│ │ value        │ │
    │  │ body mass index  │ │ measurement  │ │ compared     │ │
    │  │ number, heart    │ │              │ │ with an      │ │
    │  │ rate, blood      │ │              │ │ expected     │ │
    │  │ oxygen level, or │ │              │ │ parameter    │ │
    │  │ blood pressure   │ │              │ │ value        │ │
    │  │ proximate to     │ │              │ │              │ │
    │  │ administration   │ │              │ │              │ │
    │  │ of the bioactive │ │              │ │              │ │
    │  │ agent            │ │              │ │              │ │
    │  └──────────────────┘ └──────────────┘ └──────────────┘ │
    └─────────────────────────────────────────────────────────┘

2220
presenting an indication of an inhalation device-dispensed
bioactive agent at least partially based on the indication of the
individual's compliance with the artificial sensory experience
                                │
                                ▼
                             Finish
```

Start

2210
monitoring at least one health attribute of an individual during an artificial sensory experience

2220
presenting an indication of an inhalation device-dispensed bioactive agent at least partially based on the indication of the individual's compliance with the artificial sensory experience

| 2802 presenting an identification of a prescribed inhalation device-dispensed bioactive agent | 2804 presenting at least one effect of the inhalation device-dispensed bioactive agent in near real time | 2806 indicating at least one side effect of the inhalation device-dispensed bioactive agent |

Finish

FIG. 28

```
                    ┌─────────┐
                    │  Start  │         ← 2200
                    └────┬────┘
                         │
┌────────────────────────┴──────────────────────────────┐
│ 2210                                                   │
│ accepting an indication of an individual's compliance  │
│ with an artificial sensory experience                  │
└────────────────────────┬──────────────────────────────┘
                         │
┌────────────────────────┴──────────────────────────────┐
│ 2220                                                   │
│ presenting an indication of an inhalation device-      │
│ dispensed bioactive agent at least partially based on  │
│ the indication of the individual's compliance with the │
│ artificial sensory experience                          │
│  ┌──────────────────────────────────────────────────┐  │
│  │ 2902                                             │  │
│  │ utilizing an algorithm configured for            │  │
│  │ recommending the inhalation device-dispensed     │  │
│  │ bioactive agent                                  │  │
│  │  ┌──────────────────────┐  ┌──────────────────┐  │  │
│  │  │ 2904                 │  │ 2906             │  │  │
│  │  │ utilizing an         │  │ utilizing an     │  │  │
│  │  │ algorithm configured │  │ algorithm        │  │  │
│  │  │ for comparing at     │  │ configured for   │  │  │
│  │  │ least one effect of  │  │ identifying a    │  │  │
│  │  │ the inhalation       │  │ contraindication │  │  │
│  │  │ device-dispensed     │  │ of the           │  │  │
│  │  │ bioactive agent with │  │ inhalation       │  │  │
│  │  │ at least one         │  │ device-dispensed │  │  │
│  │  │ expected behavior of │  │ bioactive agent  │  │  │
│  │  │ the individual at    │  │                  │  │  │
│  │  │ one or more times    │  │                  │  │  │
│  │  │ proximate to the     │  │                  │  │  │
│  │  │ individual's use of  │  │                  │  │  │
│  │  │ the artificial       │  │                  │  │  │
│  │  │ sensory experience   │  │                  │  │  │
│  │  └──────────────────────┘  └──────────────────┘  │  │
│  └──────────────────────────────────────────────────┘  │
└────────────────────────┬──────────────────────────────┘
                         │
                    ┌────┴────┐
                    │ Finish  │
                    └─────────┘
```

FIG. 29

```
                    ┌─────────┐
                    │  Start  │         2200
                    └────┬────┘      ↙
                         │
┌────────────────────────┴──────────────────────────────────┐
│ 2210                                                       │
│ accepting an indication of an individual's compliance with │
│ an artificial sensory experience                           │
└────────────────────────┬──────────────────────────────────┘
                         │
┌────────────────────────┴──────────────────────────────────┐
│ 2220                                                       │
│ presenting an indication of an inhalation device-dispensed │
│ bioactive agent at least partially based on the indication │
│ of the individual's compliance with the artificial sensory │
│ experience                                                 │
└────────────────────────────────────────────────────────────┘
```

| 3002 indicating at least one of a recommended dosage or a recommended delivery method | 3004 utilizing an algorithm configured for matching at least one detected physiologic attribute of the individual with a prescription inhalation device-dispensed medication at a time proximate to the individual's use of the artificial sensory experience | 3006 determining a compatibility between the artificial sensory experience and the inhalation device-dispensed bioactive agent using at least one of a medical history, experimental data, or a medical reference book |

```
                    ┌─────────┐
                    │ Finish  │
                    └─────────┘
```

FIG. 30

```
                    ┌─────────┐
                    │  Start  │      ← 2200
                    └────┬────┘
                         │
┌────────────────────────┴─────────────────────────────┐
│ 2210                                                  │
│ accepting an indication of an individual's compliance │
│ with an artificial sensory experience                 │
└────────────────────────┬─────────────────────────────┘
                         │
┌────────────────────────┴──────────────────────────────┐
│ 2220                                                   │
│ presenting an indication of an inhalation device-      │
│ dispensed bioactive agent at least partially based on  │
│ the indication of the individual's compliance with the │
│ artificial sensory experience                          │
│  ┌──────────────────────────────────────────────────┐  │
│  │ 3202                                             │  │
│  │ presenting the indication to a third party       │  │
│  │  ┌──────────────────┐  ┌──────────────────────┐  │  │
│  │  │ 3204             │  │ 3206                 │  │  │
│  │  │ presenting the   │  │ selectively          │  │  │
│  │  │ indication to a  │  │ presenting the       │  │  │
│  │  │ health care      │  │ indication only to   │  │  │
│  │  │ provider         │  │ the individual       │  │  │
│  │  └──────────────────┘  └──────────────────────┘  │  │
│  └──────────────────────────────────────────────────┘  │
└────────────────────────┬──────────────────────────────┘
                         │
                    ┌────┴────┐
                    │ Finish  │
                    └─────────┘
```

FIG. 32

```
┌─────────────────────────────────────────────┐
│ 2210                                        │
│ accepting an indication of an individual's  │
│ compliance with an artificial sensory       │
│ experience                                  │
└─────────────────────────────────────────────┘
```

2200

Start → 2210 → 2220 → Finish

2220 presenting an indication of an inhalation device-dispensed bioactive agent at least partially based on the indication of the individual's compliance with the artificial sensory experience > 3302
> accepting a self report by an individual of compliance with a prescription for a virtual world configured to reduce breathing difficulty and presenting a prescribed dosage for an inhaler-dispensed bronchodilator at least partly based on the self report

FIG. 33

METHODS AND SYSTEMS FOR PRESENTING AN INHALATION EXPERIENCE

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

Related Applications

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Dec. 30, 2008, application Ser. No. 12/317,934, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Dec. 31, 2008, application Ser. No. 12/319,143, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Feb. 12, 2009, application Ser. No. 12/378,284, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Feb. 13, 2009, application Ser. No. 12/378,485, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Feb. 20, 2009, application Ser. No. 12/380,013, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Feb. 23, 2009, application Ser. No. 12/380,108, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Feb. 27, 2009, application Ser. No. 12/380,587, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Mar. 2, 2009, application Ser. No. 12/380,679, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Mar. 25, 2009, application Ser. No. 12/383,509, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Mar. 26, 2009, application Ser. No. 12/383,819, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD;

ELIZABETH A. SWEENEY; CLARENCE T. TEGREENE; AND LOWELL L. WOOD as inventors, filed Mar. 31, 2009, application Ser. No. 12/384,104, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Apr. 1, 2009, application Ser. No. 12/384,203, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Apr. 20, 2009, application Ser. No. 12/386,574, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Apr. 21, 2009, application Ser. No. 12/386,669, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

This description relates to methods and systems for an inhaled bioactive agent combined with an artificial sensory experience.

SUMMARY

In one aspect, a method includes but is not limited to accepting an indication of an individual's compliance with an artificial sensory experience and presenting an indication of an inhalation device-dispensed bioactive agent at least partially based on the indication of the individual's compliance with the artificial sensory experience. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In one aspect, a system includes but is not limited to means for accepting an indication of an individual's compliance with an artificial sensory experience and means for presenting an indication of an inhalation device-dispensed bioactive agent at least partially based on the indication of the individual's compliance with the artificial sensory experience. In addition to the foregoing, other method aspects are described in the claims, drawings, and text forming a part of the present disclosure.

In one aspect, a system includes but is not limited to circuitry for accepting an indication of an individual's compliance with an artificial sensory experience and circuitry for presenting an indication of an inhalation device-dispensed bioactive agent at least partially based on the indication of the individual's compliance with the artificial sensory experience. In addition to the foregoing, other method aspects are described in the claims, drawings, and text forming a part of the present disclosure.

In one aspect, a computer program product includes but is not limited to a signal-bearing medium bearing one or more instructions for accepting an indication of an individual's compliance with an artificial sensory experience and one or more instructions for presenting an indication of an inhalation device-dispensed bioactive agent at least partially based on the indication of the individual's compliance with the artificial sensory experience. In addition to the foregoing, other method aspects are described in the claims, drawings, and text forming a part of the present disclosure.

In one aspect, a system includes but is not limited to a computing device and instructions that when executed on the computing device cause the computing device to accept an indication of an individual's compliance with an artificial sensory experience and present an indication of an inhalation device-dispensed bioactive agent at least partially based on the indication of the individual's compliance with the artificial sensory experience. In addition to the foregoing, other method aspects are described in the claims, drawings, and text forming a part of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advan-

BRIEF DESCRIPTION OF THE FIGURES

FIG. 6 illustrates an operational flow representing example operations related to combining an inhaled bioactive agent and an artificial sensory experience.

FIG. 7 illustrates an alternative embodiment of the operational flow of FIG. 6.

FIG. 9 illustrates an alternative embodiment of the operational flow of FIG. 6.

FIG. 11 illustrates an alternative embodiment of the operational flow of FIG. 6.

FIG. 13 illustrates an alternative embodiment of the operational flow of FIG. 6.

FIG. 22 illustrates an operational flow representing example operations related to combining an inhaled bioactive agent and an artificial sensory experience.

FIG. 24 illustrates an alternative embodiment of the operational flow of FIG. 22.

FIG. 25 illustrates an alternative embodiment of the operational flow of FIG. 22.

FIG. 27 illustrates an alternative embodiment of the operational flow of FIG. 22.

FIG. 28 illustrates an alternative embodiment of the operational flow of FIG. 22.

FIG. 29 illustrates an alternative embodiment of the operational flow of FIG. 22.

FIG. 30 illustrates an alternative embodiment of the operational flow of FIG. 22.

FIG. 32 illustrates an alternative embodiment of the operational flow of FIG. 22.

FIG. 33 illustrates an alternative embodiment of the operational flow of FIG. 22.

DETAILED DESCRIPTION

Figure 1:
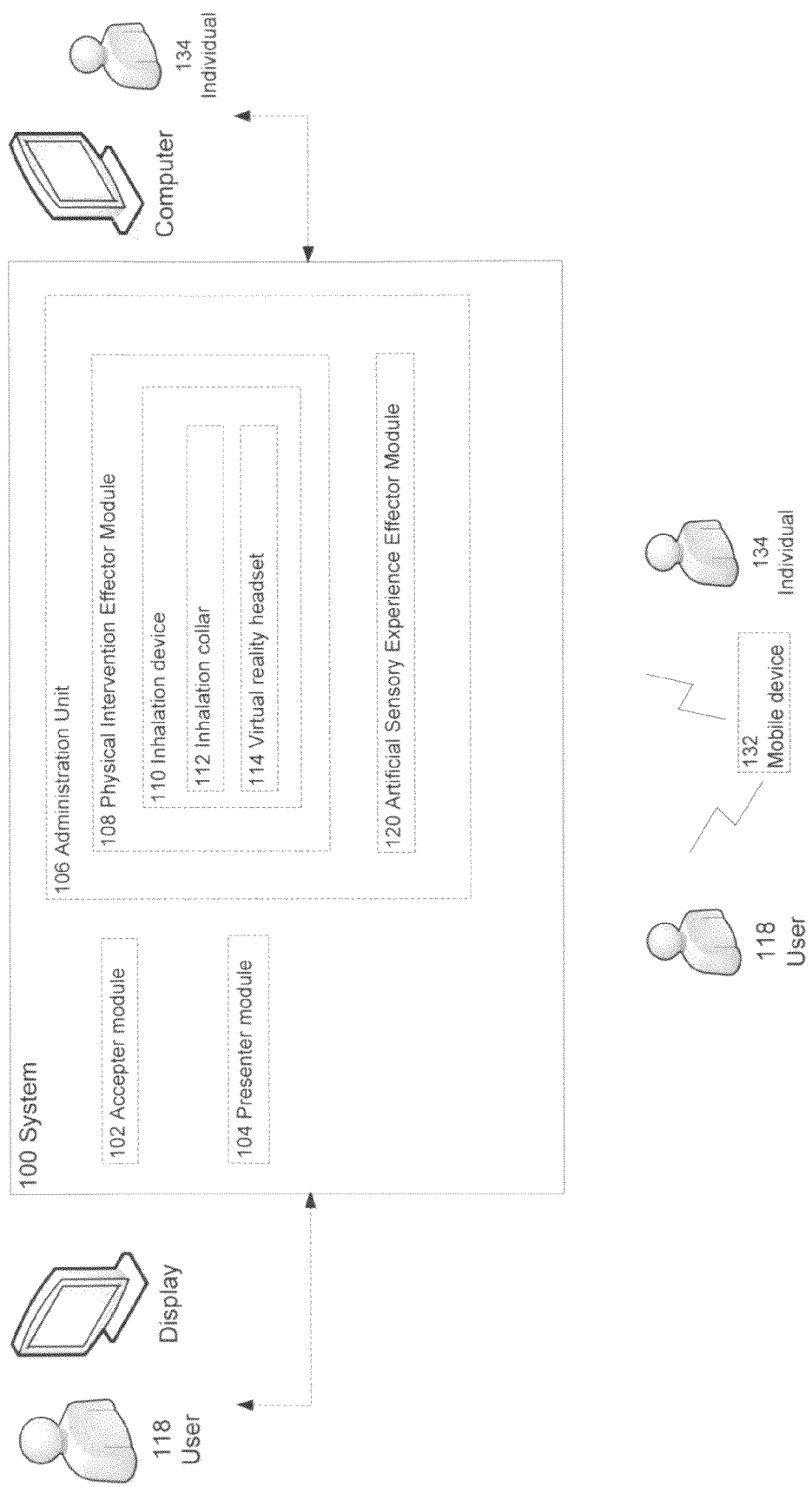
FIG. 1 illustrates an exemplary environment in which one or more technologies may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates system 100 for accepting an indication of at least one health-related condition and/or presenting an indication of at least one artificial sensory experience and an indication of at least one inhalation therapy at least partially based on the accepting at least one indication of a health-related condition. The system 100 may include accepter module 102, presenter module 104, and/or administration unit 106. Administration unit 106 may include physical intervention effector module 108 and/or artificial sensory experience effector module 120. Physical intervention effector module 108 may include inhalation device 110. Inhalation device 110 may include inhalation collar 112 and/or virtual reality headset 114. Additionally, system 3200 may include mobile device 132.

Figure 2:
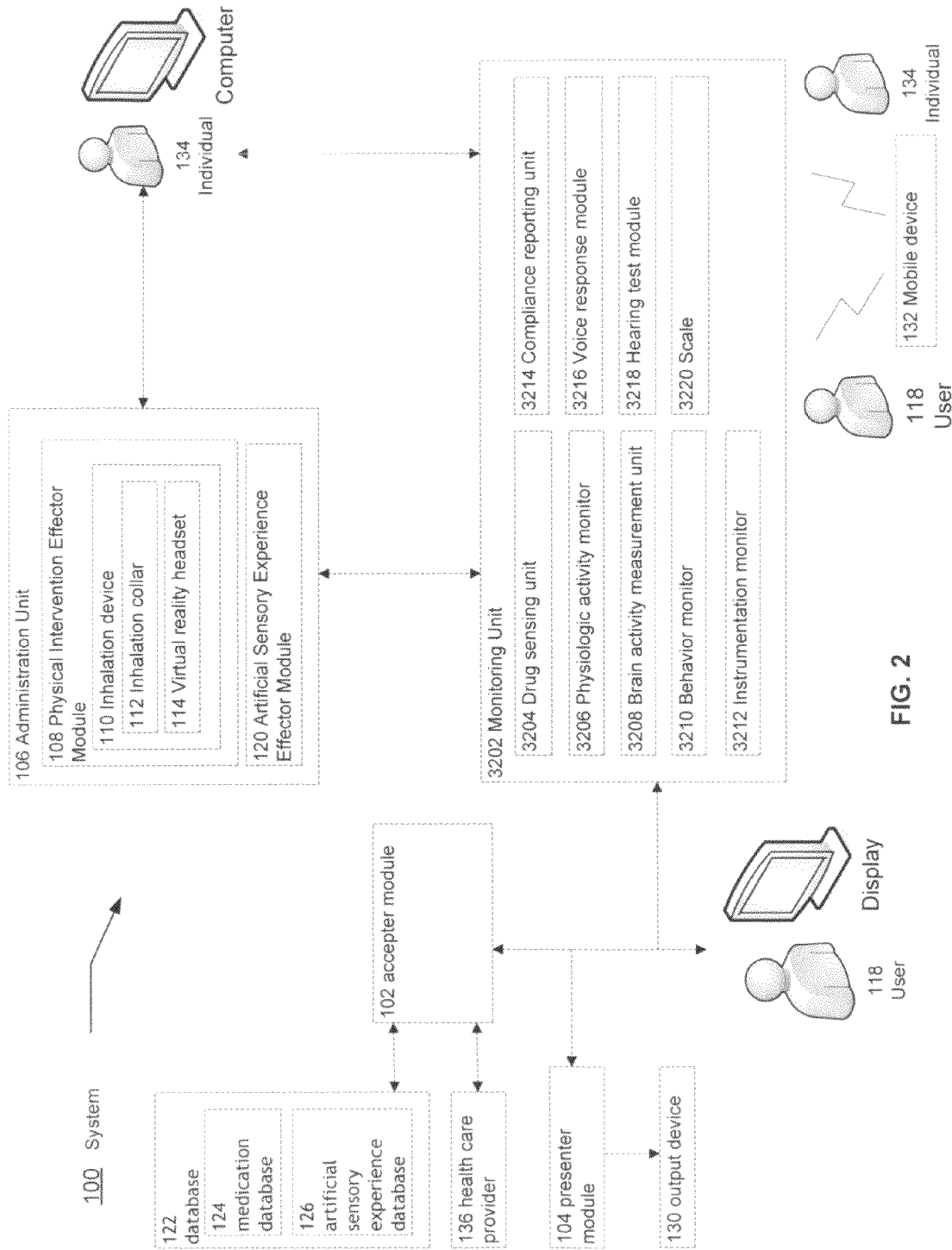
FIG. 2 illustrates an exemplary environment in which one or more technologies may be implemented.

FIG. 2 illustrates system 100 for accepting an indication of at least one health-related condition and/or presenting an indication of at least one artificial sensory experience and an indication of at least one inhalation therapy at least partially based on the accepting at least one indication of a health-related condition. The system 100 may include accepter module 102, presenter module 104, administration unit 106, and/or monitoring unit 3202. Accepter module 102 may receive and/or transmit information and/or data to and/or from user 118, database 122, presenter module 3410, output device 130, and/or health care provider 136. Database 122 may include medication database 124 and/or artificial sensory experience database 126. Monitoring unit 3202 may monitor individual 134 and may include drug sensing unit 3204, physiologic activity monitor 3206, brain activity measurement unit 3208, behavior monitor 3210, instrumentation monitor 3212, compliance reporting unit 3214, voice response module 3216, hearing test module 3218, and/or scale 3220. Administration unit 106 may include physical intervention effector module 108 and/or artificial sensory experience effector module 120. Physical intervention effector module 108 may include inhalation device 110. Inhalation device 110 may include inhalation collar 112 and/or virtual reality headset 114. Additionally, mobile device 132 may communicate with accepter module 102, presenter module 104, healthcare provider 136, user 118, individual 134, monitoring unit 3202, and/or administration unit 3222.

Figure 3:
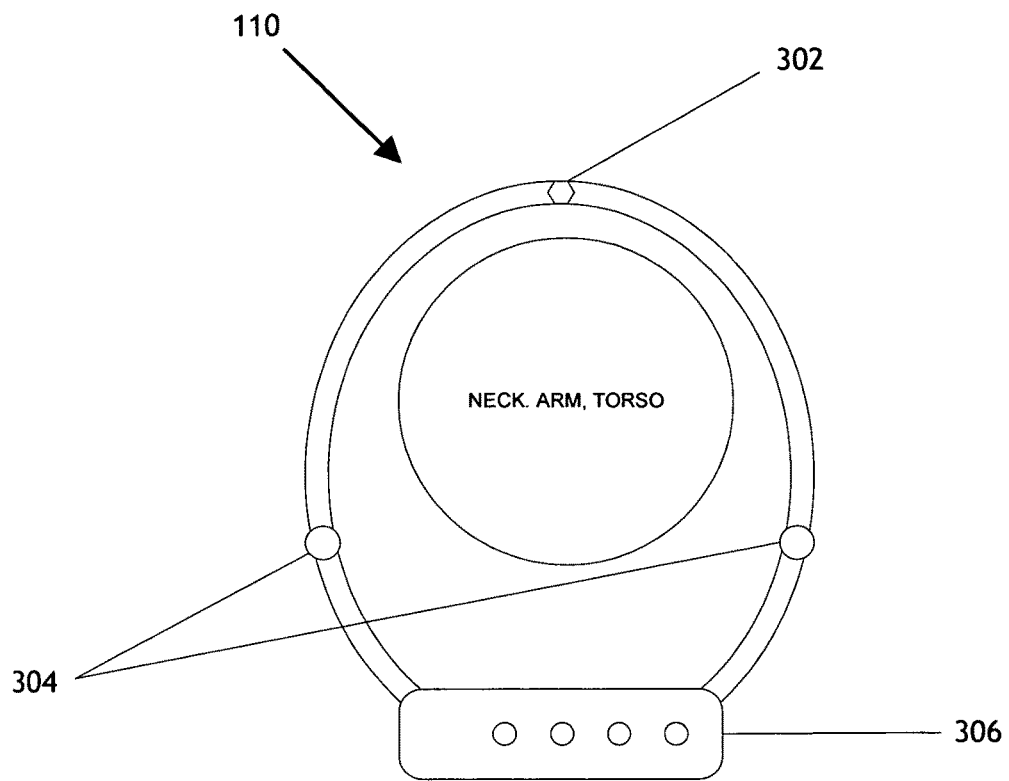
FIG. 3 illustrates an exemplary inhalation device.

FIG. 3 illustrates an exemplary inhalation device 110. An exemplary inhalation device 110 may include a closure device, a transducer, and/or a dispensing reservoir. Inhalation device 110 may include, for example, a collar, a necklace, and/or a bracelet. Inhalation device 110 may include tubing, a chain, a polymer, a metal, a textile, and may be solid and/or hollow. Closure device 302 may include a buckle, Velcro, a snap, a clasp, a lock, a coupler, elastic, and/or magnets. Transducer 304 may include a blood glucose monitor, a blood oxygen monitor, means for sending a signal to a reservoir to dispense medication, such as an antenna, means for powering the unit, such as a battery, memory, and/or a computer processor. Dispensing reservoir 306 may include means for power, such as a battery, means for receiving conditional input, such as a processor and/or memory, means for dispensing a bioactive agent in aerosol, dust and/or vapor form, such as a nebulizer, a sprayer, and/or a nozzle. Additionally, the dispensing reservoir 306 may be removable and/or refillable.

Figure 4:
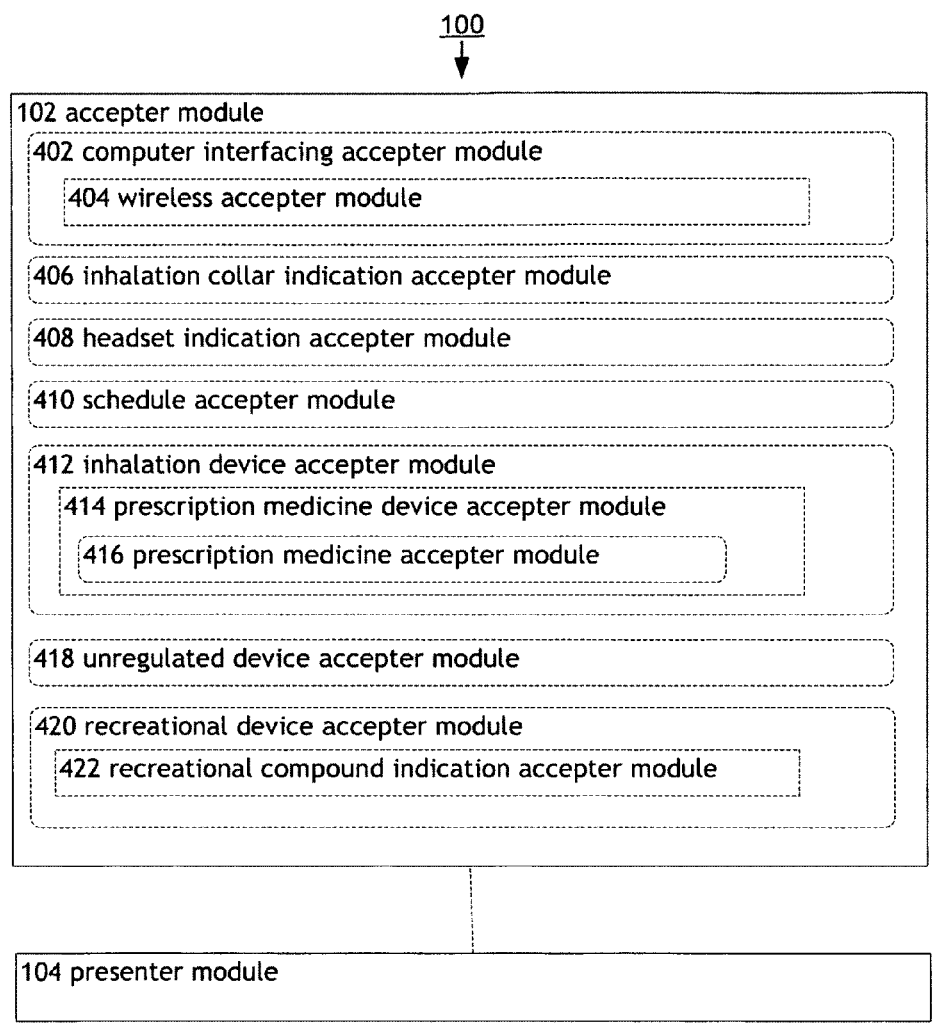
FIG. 4 illustrates an exemplary environment in which one or more technologies may be implemented.

FIG. 4 further illustrates system 100 including accepter module 102 and/or presenter module 104. Accepter module 102 may include computer interfacing accepter module 402, inhalation collar indication accepter module 406, headset indication accepter module 408, schedule accepter module 410, inhalation device accepter module 412, unregulated device accepter module 418, and/or recreational device accepter module 420. Computer interfacing accepter module 402 may include wireless accepter module 404. Inhalation device accepter module 412 may include prescription medicine device accepter module 414 and/or prescription medicine accepter module 416. Recreational device accepter module 420 may include recreational compound indication accepter module 422.

Figure 5:
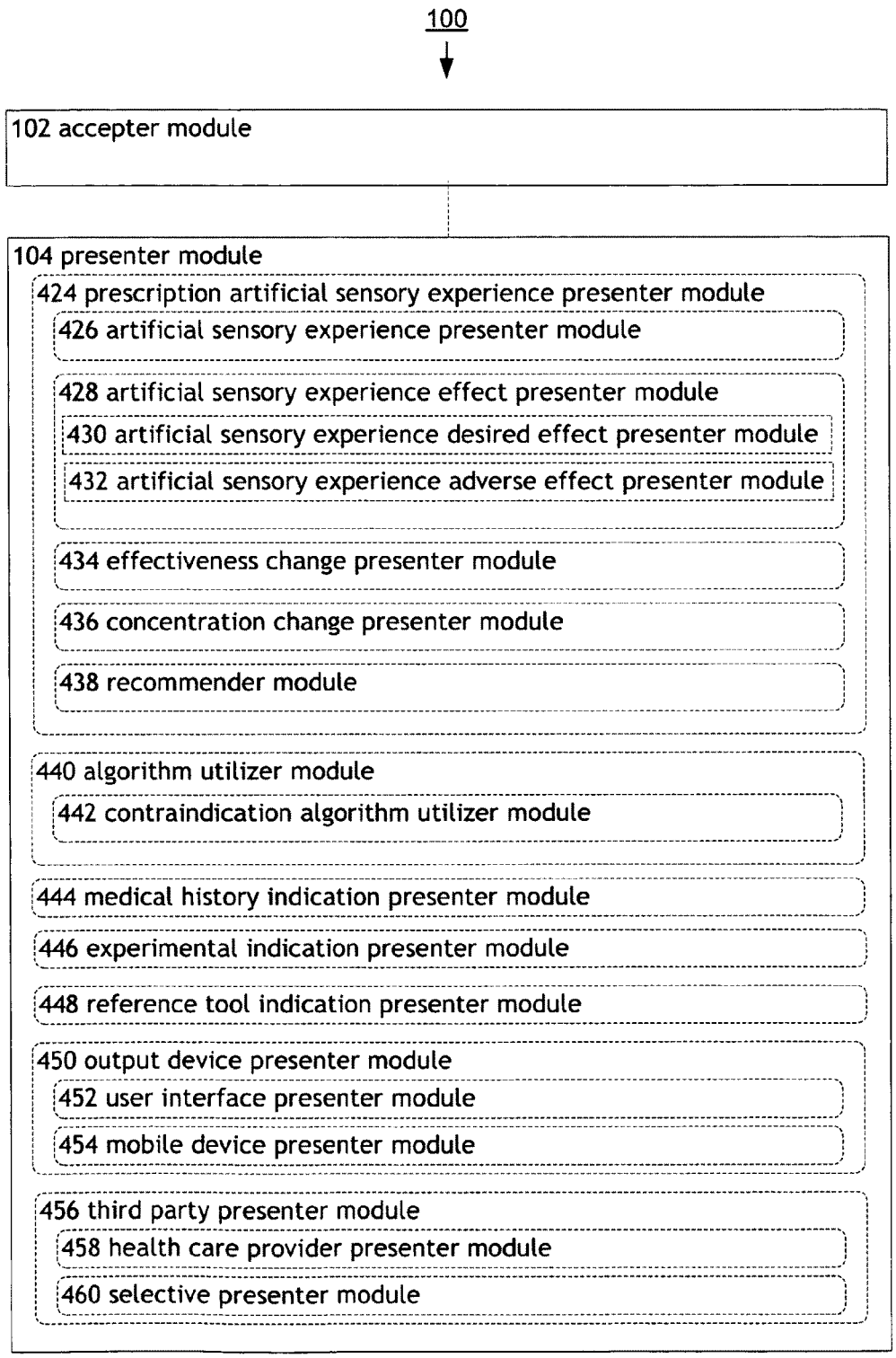
FIG. 5 illustrates an exemplary environment in which one or more technologies may be implemented.

FIG. 5 illustrates system 100 including accepter module 102 and/or presenter module 104. Presenter module 104 may include prescription artificial sensory experience presenter module 424, algorithm utilizer module 440, medical history indication presenter module 444, experimental indiciation presenter module 446, reference tool indication presenter module 448, output device presenter module 450, and/or third party presenter module 456. Prescription artificial sensory experience presenter module 424 may include artificial sensory experience presenter module 426, artificial sensory experience effect presenter module 428, effectiveness change presenter module 434, concentration change presenter module 436, and/or recommender module 438. Artificial sensory experience effect presenter module 428 may include artificial sensory experience desired effect presenter module 430 and/or artificial sensory experience adverse effect presenter module 432. Algorithm utilizer module 440 may include contraindication algorithm utilizer module 442. Output device presenter module 450 may include user interface presenter module 452 and/or mobile device presenter module 454. Third party presenter module 456 may include health care provider presenter module 458 and/or selective presenter module 460.

FIG. 6 illustrates an operational flow 600 representing example operations related to accepting an indication of at least one health-related condition and presenting an indication of at least one artificial sensory experience and an indication of at least one inhalation therapy at least partially based on the accepting at least one indication of a health-related condition. In FIG. 6 and in following figures that include various examples of operational flows, discussion and explanation may be provided with respect to the above-described examples of FIGS. 1 through 5, and/or with respect to other examples and contexts. However, it should be understood that the operational flows may be executed in a number of other environments and contexts, and/or in modified versions of FIGS. 1 through 5. Also, although the various operational flows are presented in the sequence(s) illustrated, it should be understood that the various operations may be performed in other orders than those which are illustrated, or may be performed concurrently.

After a start operation, the operational flow 600 moves to operation 610. Operation 610 depicts accepting an indication of at least one health-related condition. For example, as shown in FIGS. 1 through 5, accepter module 102 may accept an indication of a bioactive agent-dispensing inhalation device. One example of a bioactive agent-dispensing inhalation device may include an inhaler used for delivering a bioactive agent into the body using a body airway. Some other examples may include a collar, necklace, and/or a bracelet with a bioactive agent dispenser proximate to the nose, mouth, and/or inhalation route. In one embodiment, accepter module 102 may accept an indication of a bioactive agent-dispensing collar for dispensing a medication, such as a steroid and/or a bronchodilator. In some instances, accepter module 102 may include a computer processor, a user interface, and/or computer memory.

Then, operation 620 depicts presenting an indication of at least one artificial sensory experience and an indication of at least one inhalation therapy at least partially based on the accepting at least one indication of a health-related condition. For example, as shown in FIGS. 1 through 5, presenter module 104 may present an indication of a virtual world at least partially based on accepting an indication of a bioactive agent-dispensing inhalation device. One example of an artificial sensory experience may include a virtual world and/or other computer-simulated experience. Other examples of an artificial sensory experience may include experiences triggering sight, smell, hearing, touch, and/or taste. For example, presenter module 104 may present an indication of an artificial sensory experience including a virtual scent environment, which may include olfactory stimulation for improving memory. In an additional embodiment, presenter module 104 may present an indication of an artificial sensory experience including a virtual experience where the user is exposed to a virtual mountain environment coupled with a bronchodilator dose from a bioactive agent-dispensing inhalation collar. In this embodiment, the combination bronchodilator and virtual world treatment may serve to help an asthma sufferer to learn effective breathing techniques. Presenting an indication of an artificial sensory experience may include presenting the indication to a physician, to a computer monitor, to a mobile device, and/or to a third party. In some instances, presenter module 104 may include a computer processor and/or a communication device, such as a printer, a computer monitor, and/or a speaker.

FIG. 7 illustrates alternative embodiments of the example operational flow 600 of FIG. 6. FIG. 7 illustrates example embodiments where operation 610 may include at least one additional operation. Additional operations may include operation 702, operation 704, operation 706, and/or operation 708.

Operation 702 illustrates accepting an indication of a health-related physical condition. For example, as shown in FIGS. 1 through 5, computer interfacing accepter module 402 may accept an indication of a bioactive agent-dispensing inhalation device configured to interface with a computing device. In one embodiment, computer interfacing accepter module 402 may accept an indication of a bioactive agent-dispensing inhalation device configured to interface with a virtual game, such as World of Warcraft. Some examples of a computing device may include a personal computer, a virtual-reality helmet and/or headset, and/or a virtual environment. In some instances, computer interfacing accepter module 402 may include a computer processor.

Further, operation 704 illustrates accepting an indication of a bioactive agent-dispensing inhalation device configured to interface wirelessly with a computing device. For example, as shown in FIGS. 1 through 5, wireless accepter module 404 may accept an indication of a bioactive agent-dispensing inhalation device configured to interface wirelessly with a computing device. In one embodiment, wireless accepter module 404 may accept an indication of a wireless inhalation collar configured to interface wirelessly with a computer coupled to wireless video glasses. In this embodiment, both the inhalation collar and the video glasses may be wirelessly connected to the computer. The wireless bioactive agent-dispensing inhalation device may be wirelessly coupled to a computing device using, for example, an IEEE 802.11 computer network and/or a Bluetooth wireless sensor network. One example of wireless video glasses may include Qingbar GP300 video glasses available from 22moo International Pty Ldt., Cabramatta NSW, Australia. In some instances, wireless accepter module 404 may include a computer processor and/or a wireless receiving device, such as a receiving antenna.

Operation 706 illustrates accepting an indication a health-related condition from a medical history. For example, as shown in FIGS. 1 through 5, inhalation collar indication accepter module 406 may accept an indication of a bioactive agent-dispensing inhalation collar. A bioactive agent-dispensing inhalation collar may include a collar with, for example, means for dispensing a bioactive agent, such as a reservoir and/or an accompanying valve and spray nozzle. Additionally, means for dispensing a bioactive agent may include means for dispensing an aerosol, vapor, a powder (e.g. pulmicort and/or foradil), and/or a mist, such as a nebulizer, means for measuring and/or detecting a condition, such as blood oxygen level and/or body temperature, and/or means for processing information, such as a computer processor and/or computer memory. Further, a bioactive agent may be dispensed and/or dispersed in and/or include a surfactant. In one embodiment, inhalation collar indication accepter module 406 may accept an indication of a bioactive agent-dispensing collar having means for dispensing a steroid as an aerosol. Further, a bioactive agent-dispensing inhalation collar may include means for power, such as a battery and/or circuitry for receiving power from an external source, such as an AC adapter power supply. In some instances, inhalation collar indication accepter module 406 may include a computer processor.

Operation 708 illustrates accepting an indication of a bioactive agent-dispensing virtual-reality headset. For example, as shown in FIGS. 1 through 5, headset indication accepter module 408 may accept an indication of a bioactive agent-dispensing virtual-reality headset. A virtual-reality headset may include a microphone, headphones or speakers for hearing, and/or a display. A virtual-reality headset may be configured for enabling a user to engage in an artificial sensory experience including sound, smell, and/or sight. One example of a virtual-reality headset may include a virtual reality helmet configured to give the user a 360° view of a mountain landscape while dispensing a bronchodilator for helping the user learn improved breathing techniques. Another example of a virtual reality head set may include an Olympus Eye-Trek FMD-200—TFT active matrix head mounted display with Speaker, available from Olympus America Inc., Center Valley Pa. In some instances, headset indication accepter module 408 may include a computer processor.

Figure 8:
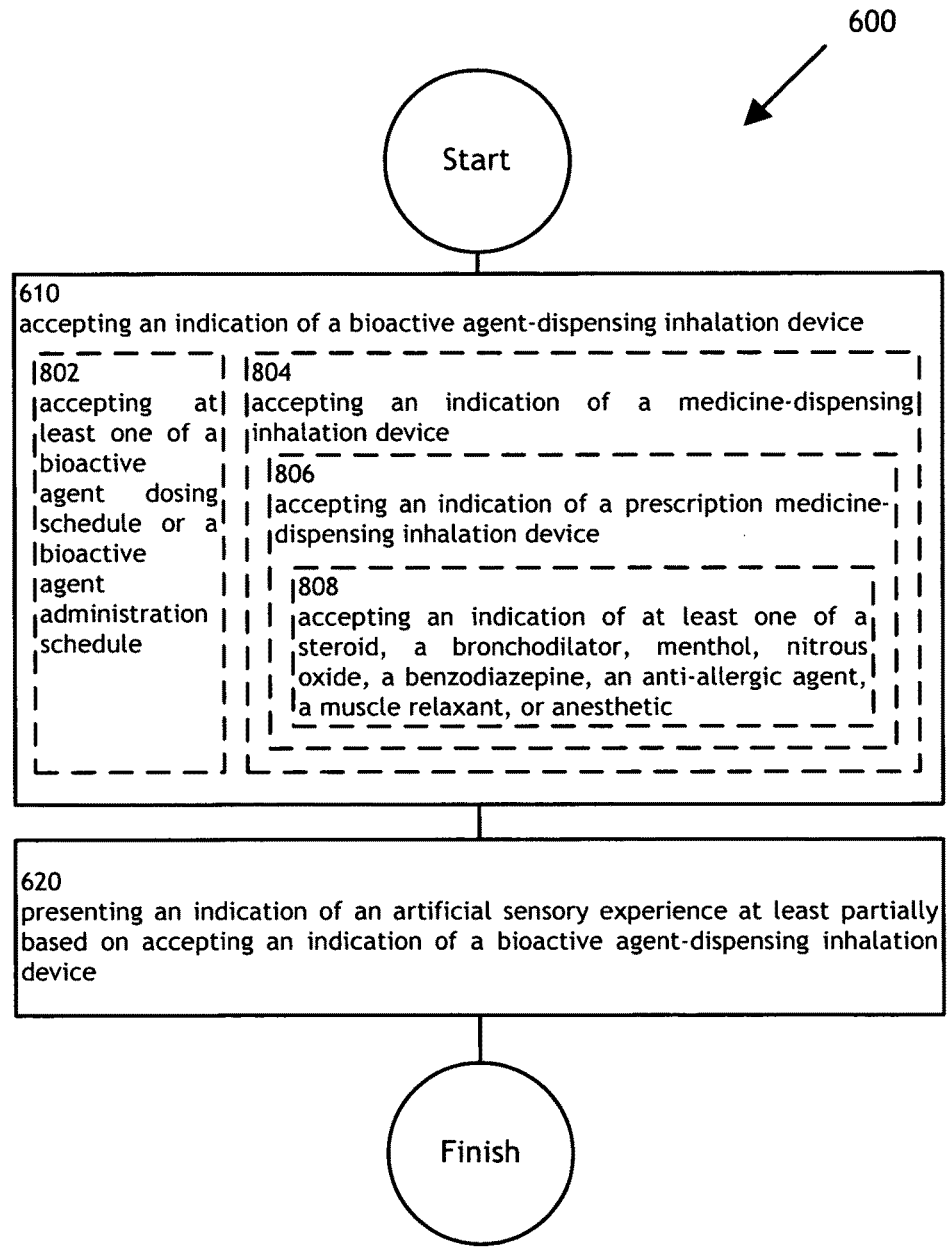
FIG. 8 illustrates an alternative embodiment of the operational flow of FIG. 6.

FIG. 8 illustrates alternative embodiments of the example operational flow 600 of FIG. 6. FIG. 8 illustrates example embodiments where the operation 610 may include at least one additional operation. Additional operations may include an operation 802, an operation 804, an operation 806, and/or an operation 808.

Operation 802 illustrates accepting an indication of a health-related mental condition. For example, as shown in FIGS. 1 through 5, schedule accepter module 410 may accept at least one of a bioactive agent dosing schedule or a bioactive agent administration schedule. Accepting a bioactive agent dosing schedule or a bioactive agent administration schedule may include accepting from a computer processor, accepting from a memory device, and/or accepting from a user input. In one embodiment, schedule accepter module 410 may accept a dosing schedule specifying a bronchodilator administration dosage for a specified time period, such one dose from an inhalation device once every thirty minutes. In another embodiment, schedule accepter module 410 may accept a bioactive agent administration schedule specifying at least one time a bronchodilator may be administered. In some instances, schedule accepter module 410 may include a computer processor.

Operation 804 illustrates accepting an indication of a medicine-dispensing inhalation device. For example, as shown in FIGS. 1 through 5, inhalation device accepter module 412 may accept an indication of a medicine-dispensing inhalation device. A medicine-dispensing inhalation device may include a device for dispensing a substance for treating a disease and/or illness. For example, a medicine-dispensing inhalation device may include an inhaler as described in Robertson et al., U.S. Pat. No. 7,383,837, which is incorporated herein by reference. Some other examples may include a metered-dose inhaler, a dry powder inhaler, and/or a nebulizer. In one embodiment, inhalation device accepter module 412 may accept an indication of a medicine-dispensing metered-dose inhaler configured to dispense albuterol. In some instances, inhalation device accepter module 412 may include a computer processor.

Further, operation 806 illustrates accepting an indication of a health-related condition from a user input. For example, as shown in FIGS. 1 through 5, prescription medicine device accepter module 414 may accept an indication of a prescription medicine-dispensing inhalation device. A prescription medicine-dispensing inhalation device may include a device configured to dispense a medication only available from a licensed health care provider. Some examples of a prescription medication available from a licensed health care provider may include albuterol, coricosteroids, nitrous oxide, a benzodiazepine, Theophylline, nedocromil sodium, and/or fluticasone/salmeterol. In one embodiment, prescription medicine device accepter module 414 may accept an indication of a prescription medicine-dispensing inhalation device configured for dispensing ciclesonide. In some instances, prescription medicine device accepter module 414 may include a computer processor.

Further, operation 808 illustrates indication of at least one of a prescribed artificial sensory experience or a prescribed inhalation therapy. For example, as shown in FIGS. 1 through 5, prescription medicine accepter module 416 may accept an indication of at least one of a steroid, a bronchodilator, menthol, nitrous oxide, a benzodiazepine, or halothane. One example of a steroid may include an anabolic steroid, which may be a derivative of androgens (such as testosterone), for stimulating growth. Another example of a steroid may include a corticosteroid, which may be often used as an anti-inflammatory prescribed for asthma. A bronchodilator may include a substance that dilates the bronchi and bronchioles decreasing airway resistance and thereby facilitating airflow. Menthol may include an organic and/or synthetic compound with local anesthetic and counterirritant qualities often used for relieving throat irritation and/or as a decongestant. Nitrous oxide may include a gas often used as a weak general anesthetic. A benzodiazepine may include a class of psychoactive drugs with varying hypnotic, sedative, anxiolytic, anticonvulsant, muscle relaxant and amnesic properties, which may be mediated by slowing down the central nervous system. In one embodiment, prescription medicine accepter module 416 may accept an indication of a benzodiazepine. One example of benzodiazepine delivery through an inhalation route may be disclosed in Kim et al., U.S. Patent Publication No. 2003/0032638, which is incorporated herein by reference. An anti-allergic agent may include an agent configured to block the action of allergic mediators and/or to prevent activation of cells and degranulation processes. Some examples of an anti-allergic agent may include an antihistamine and/or cromones like mast cell stabilizers, such as cromoglicic acid and nedocromil sodium. A muscle relaxant may include a bioactive agent for affecting skeletal muscle function and/or decreasing muscle tone. One example of a skeletal muscle relaxant may include carisoprodol. Additionally, a muscle relaxant may include a smooth muscle relaxant. One example of a smooth muscle relaxant may include a methylxanthine, such as Theophylline. An anesthetic may include an inhalational general anesthetic, such as halothane, desflurane, enflurane, isoflurane, and/or sevoflurane. In some instances, prescription medicine accepter module 416 may include a computer processor.

FIG. 9 illustrates alternative embodiments of the example operational flow 600 of FIG. 6. FIG. 9 illustrates example embodiments where the operation 610 may include at least one additional operation. Additional operations may include an operation 902, an operation 904, and/or an operation 906.

Operation 902 illustrates accepting an indication of an unregulated bioactive agent-dispensing inhalation device. For example, as shown in FIGS. 1 through 5, unregulated device accepter module 418 may accept an indication of an unregulated bioactive agent-dispensing inhalation device. In one embodiment, unregulated device accepter module 418 may accept an indication of an oxygen-dispensing inhalation device. Some examples of an unregulated bioactive agent may include oxygen, aromas used for aromatherapy, and/or menthol. In another embodiment, unregulated device accepter module 418 may accept an indication of an aromatherapeutic-dispensing inhalation collar. In some instances, unregulated device accepter module 418 may include a computer processor.

Operation 904 illustrates accepting an indication of a recreational bioactive agent-dispensing inhalation device. For example, as shown in FIGS. 1 through 5, recreational device accepter module 420 may accept an indication of a recreational bioactive agent-dispensing inhalation device. In one embodiment, recreational device accepter module 420 may accept an indication of a recreational bioactive agent-dispensing inhalation device. Some examples of a recreational bioactive agent may include an aroma compound used for aromatherapy and/or artificial smoke. Other examples of a recreational bioactive agent may include incense and/or smoke, such as incense and/or smoke used in a religious rite. In some instances, recreational device accepter module 420 may include a computer processor.

Further, operation 906 illustrates accepting an indication of at least one artificial smoke or an aroma compound. For example, as shown in FIGS. 1 through 5, recreational compound indication accepter module 422 may accept an indication of at least one artificial smoke or an aroma compound. In one embodiment, recreational compound indication accepter module 422 may accept an indication of artificial smoke while experiencing a virtual world. In another embodiment, recreational compound indication accepter module 422 may accept an indication of lemon oil while experiencing an artificial sensory experience. In this embodiment, the use of lemon oil as an aromatherapeutic may serve to enhance a user's mood and/or provide relaxation. In some instances, recreational compound indication accepter module 422 may include a computer processor.

Figure 10:
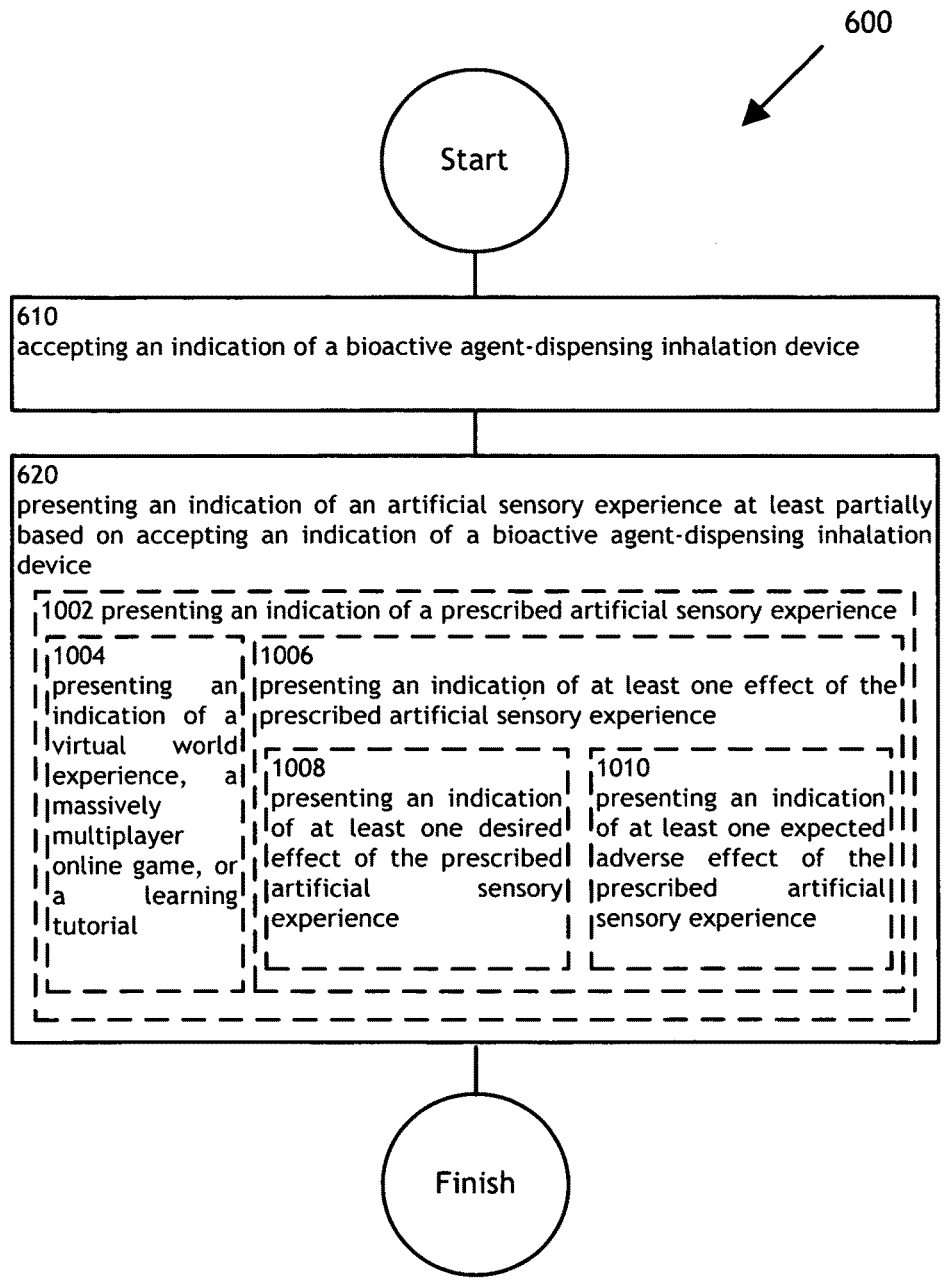
FIG. 10 illustrates an alternative embodiment of the operational flow of FIG. 6.

FIG. 10 illustrates alternative embodiments of the example operational flow 600 of FIG. 6. FIG. 10 illustrates example embodiments where operation 620 may include at least one additional operation. Additional operations may include operation 1002, operation 1004, operation 1006, operation 1008, and/or operation 1010.

Operation 1002 illustrates indication of at least one of a prescribed artificial sensory experience or a prescribed inhalation therapy. For example, as shown in FIGS. 1 through 5, prescription artificial sensory experience presenter module 424 may present an indication of a prescribed artificial sensory experience. A prescribed artificial sensory experience may include any artificial sensory experience prescribed by a health care professional, such as a physician, a mental health specialist, a nurse, a physical therapist, an occupational therapist, a chiropractor, and/or a homeopathic practitioner. In one embodiment, prescription artificial sensory experience presenter module 424 may present an indication of a virtual world prescribed by a psychiatrist. In this embodiment, the prescribed virtual world may be configured to be administered in conjunction with a prescribed bioactive agent. Administering a prescribed bioactive agent in conjunction with a prescribed artificial sensory experience may serve to increase efficacy of the combined therapy, for example, by serving as a distraction from pain. In some instances, prescription artificial sensory experience presenter module 424 may include a computer processor and/or a display device, such as a computer monitor and/or a printer.

Further, operation 1004 illustrates an indication of at least one of a virtual world experience, a massively multiplayer online game, or a learning tutorial. For example, as shown in FIGS. 1 through 5, artificial sensory experience presenter module 426 may present an indication of a virtual world experience, a massively multiplayer online game, or a learning tutorial. A virtual world experience may include a computer-based simulated environment intended to be interactive. Some examples of a virtual world experience may include a text-based chat room, computer conferencing, an online game, a single player game, and/or a computer tutorial. A massively multiplayer online game may include a video game capable of supporting multiple players, such as World of Warcraft and/or SecondLife. Additionally, a massively multiplayer online game may include an experience, such as a game, which may include a video game or other interactive experience involving numbers of individuals, for example, a religious ceremony or combat training exercise. An online learning tutorial may include a screen recording, a written document (either online or downloadable), or an audio file, where a user may be given step by step instructions on how to do something. In one embodiment, artificial sensory experience presenter module 426 may present an indication of a virtual world experience, such as World of Warcraft. In some instances, artificial sensory experience presenter module 426 may include a computer processor.

Further, operation 1006 illustrates indication of at least one effect of the indication of at least one of a prescribed artificial sensory experience. For example, as shown in FIGS. 1 through 5, artificial sensory experience effect presenter module 428 may present an indication of at least one effect of the prescribed artificial sensory experience. In one embodiment, artificial sensory experience effect presenter module 428 may present an indication of at least one effect of the prescribed artificial sensory experience. An effect may include a reaction and/or thing that occurs as a result of the artificial sensory experience. For example, an effect may include a side effect, a desired effect, and/or an adverse effect. Some examples of an effect may include an increased bioactive agent efficacy, dizziness, and/or a decreased heart rate. In some instances, artificial sensory experience effect presenter module 428 may include a computer processor.

Further, operation 1008 illustrates presenting an indication of at least one expected desired effect of the prescribed artificial sensory experience. For example, as shown in FIGS. 1 through 5, artificial sensory experience desired effect presenter module 430 may present an indication of at least one desired effect of the prescribed artificial sensory experience. Some examples of a desired effect may include effects such as an increased bioactive agent efficacy, a cured illness and/or condition, and/or a changed behavior. In one embodiment, artificial sensory experience desired effect presenter module 430 may present an indication of an increased opioid efficacy measured by self pain evaluation by an individual. In some instances, artificial sensory experience desired effect presenter module 430 may include a computer processor and/or a display, such as a monitor and/or a printer.

Further, operation 1010 illustrates an indication of at least one prescribed inhalation therapy. For example, as shown in FIGS. 1 through 5, artificial sensory experience adverse effect presenter module 432 may present an indication of an expected adverse effect of the prescribed artificial sensory experience. An adverse effect may include a harmful and/or undesired effect resulting from an intervention, such as an artificial sensory experience. Some examples of an adverse effect may include headache, dizziness, depression, bleeding, seizure, and/or fever. In one embodiment, artificial sensory experience adverse effect presenter module 432 may present an indication of fever in an individual while being administered a prescribed artificial sensory experience and bioactive agent. In some instances, artificial sensory experience adverse effect presenter module 432 may include a computer processor, a display device, such as a monitor and/or printer, and/or medical instrumentation, such as a thermometer configured for measuring a body temperature.

FIG. 11 illustrates alternative embodiments of the example operational flow 600 of FIG. 6. FIG. 11 illustrates example embodiments where operation 620 may include at least one additional operation. Additional operations may include operation 1102, operation 1104, and/or operation 1106.

Operation 1102 illustrates an indication of at least one prescribed bioactive agent. For example, as shown in FIGS. 1 through 5, effectiveness change presenter module 434 may present an indication of at least one time period of an expected change in bioactive agent effectiveness. In one embodiment, effectiveness change presenter module 434 may present an indication of a time period when an opioid is expected to decrease in effectiveness. Such an indication of decrease and/or change in bioactive agent effectiveness may serve to indicate an appropriate time period for administering and/or modifying an artificial sensory experience to compensate for a change in bioactive agent efficacy. In another embodiment, effectiveness change presenter module 434 may present an indication of a time period where a blood stream morphine concentration drops. This time period of low blood stream morphine concentration may be appropriate for presenting an immersive virtual world for serving as a distraction to any increase in pain caused by lowered morphine concentration. In some instances, effectiveness change presenter module 434 may include a computer processor.

Further, operation 1104 illustrates an indication of at least one time period of an expected change in bioactive agent blood concentration. For example, as shown in FIGS. 1 through 5, concentration change presenter module 436 may present an indication of at least one time period of an expected change in bioactive agent blood concentration. In one embodiment, concentration change presenter module 436 may present an indication of a one hour time period of an expected change in hydrocodone blood concentration. Indicating a time period of a change in blood concentration may serve to help determine an artificial sensory experience administration schedule. For example, if a bioactive agent blood concentration is expected to be reduced during a certain time period, an artificial sensory experience configured for distracting an individual from pain may be selected for administration during that time period. In some instances, concentration change presenter module 436 may include a computer processor and/or a display device, such as a printer and/or a computer monitor.

Further, operation 1106 illustrates recommending at least one of an artificial sensory experience administration schedule. For example, as shown in FIGS. 1 through 5, recommender module 438 may recommend an artificial sensory experience administration schedule. In one embodiment, recommender module 438 may recommend a time schedule for administration of a virtual world experience. A time schedule may be recommended by taking into account factors involving the individual and/or the bioactive agent. For example, efficacy of the bioactive agent versus time may be a factor, such as a time period when the bioactive agent is less effective. Efficacy of the bioactive agent may be a factor in determining when an artificial sensory experience is administered because of the potential for the artificial sensory experience to compensate for a changed bioactive agent efficacy. An additional factor may include an attribute of the individual, such as how a bioactive agent and/or specific artificial sensory experience affects the individual, for example a side effect. Another example of recommending an artificial sensory experience may be found in Akazawa et al., U.S. Pat. No. 7,155,680, which is incorporated herein by reference. In some instances, recommender module 438 may include a computer processor.

Figure 12:
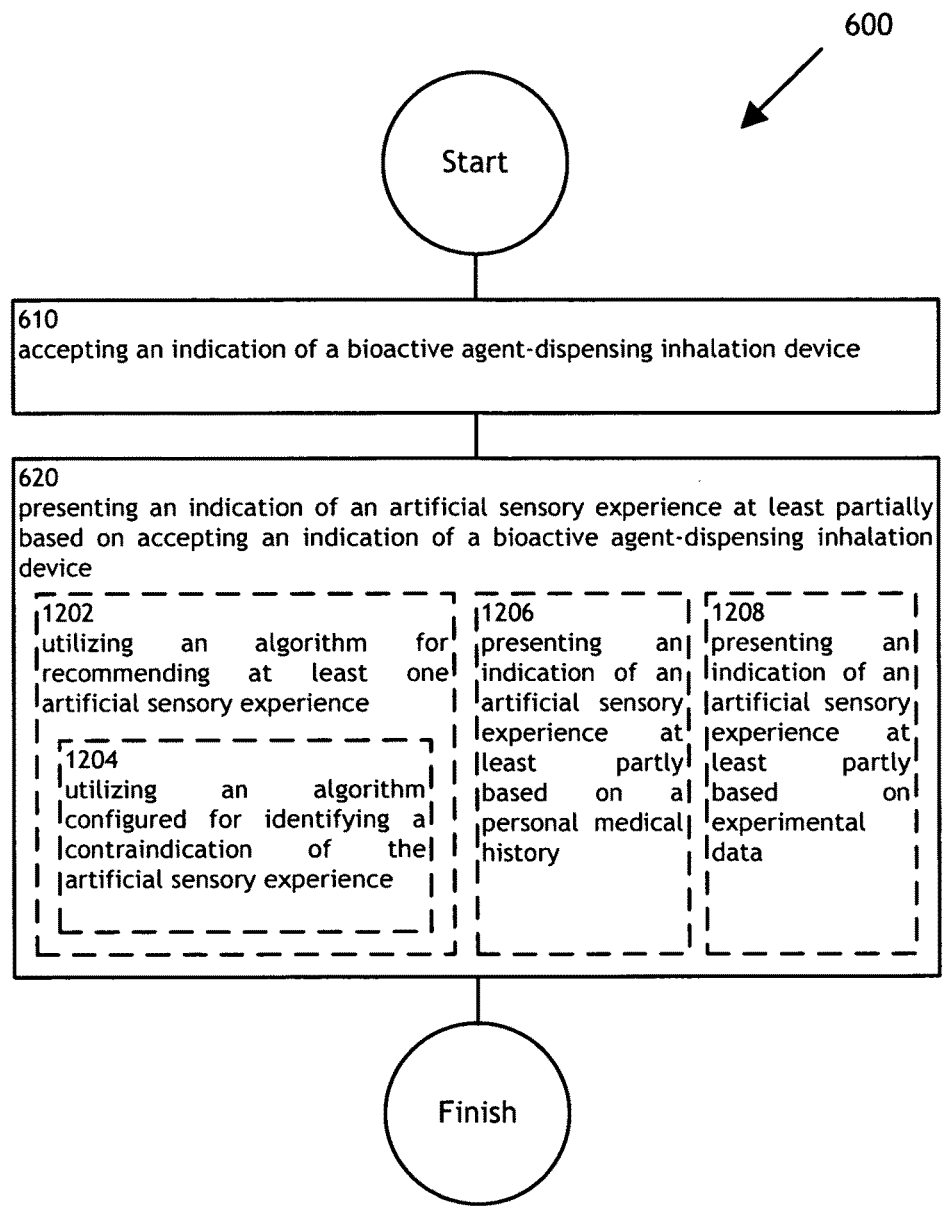
FIG. 12 illustrates an alternative embodiment of the operational flow of FIG. 6.

FIG. 12 illustrates alternative embodiments of the example operational flow 600 of FIG. 6. FIG. 12 illustrates example embodiments where operation 620 may include at least one additional operation. Additional operations may include operation 1202, operation 1204, operation 1206, and/or operation 1208.

Operation 1202 illustrates an indication of an unregulated inhalation. For example, as shown in FIGS. 1 through 5, algorithm utilizer module 440 may utilize an algorithm for recommending at least one artificial sensory experience. An algorithm for recommending an artificial sensory experience may include any computation, formula, statistical survey, and/or look-up table for determining and/or selecting a suitable artificial sensory experience. Some examples may include a computer software algorithm, a calculator, a flowchart, and/or a decision tree. In one embodiment, algorithm utilizer module 440 may utilize an algorithm that uses an inputted indication of an analgesic, such as oxycodone, and determines a suitable artificial sensory experience by analyzing periods of low blood concentration of the oxycodone. In this embodiment, algorithm utilizer module 440 may recommend an artificial sensory experience that may be effective in pain distraction when bioactive agent blood concentration may be reduced but before an additional dose may be available. In some instances, algorithm utilizer module 440 may include a computer processor.

Further, operation 1204 illustrates an indication of an unregulated inhalation. For example, as shown in FIGS. 1 through 5, contraindication algorithm utilizer module 442 may utilize an algorithm configured for identifying a contraindication of the artificial sensory experience. A contraindication of an artificial sensory experience may include giving an indication against the advisability of the artificial sensory experience. For example, contraindication algorithm utilizer module 442 may utilize an algorithm that considers an individual's personal medical history, such as a phobia, and may recommend not prescribing a certain artificial sensory experience, which may include an object that may trigger the phobia. Contraindication algorithm utilizer module 442 may identify a contraindication of an artificial sensory experience for reasons such as an adverse effect and/or inefficacy. In some instances, contraindication algorithm utilizer module 442 may include a computer processor.

Operation 1206 illustrates presenting an indication of an artificial sensory experience at least partly based on a personal medical history. For example, as shown in FIGS. 1 through 5, medical history indication presenter module 444 may present an indication of an artificial sensory experience at least partly based on a personal medical history. A medical history may include a personal history and/or a family history. A personal medical history may include a list of previous illnesses, symptoms, medicines, treatments, health risk factors, operations, and/or doctor visits associated with at least one individual. A personal and/or a family medical history may include life history and/or social history characteristics such as smoking, drinking, drug use, sexual history, exercise history, eating history, nutraceutical history, or the like. In one embodiment, medical history indication presenter module 444 may present an indication of a suitable virtual world based on a personal medical history. In this embodiment, the personal medical history may indicate that an individual may be averse to a certain virtual world, such as a virtual world with rapid animation that may cause nausea. In some instances, medical history indication presenter module 444 may include a computer processor and/or a display device, such as a computer monitor and/or a printer.

Operation 1208 illustrates utilizing an algorithm configured for recommending at least one of an artificial sensory experience. For example, as shown in FIGS. 1 through 5, experimental data indication presenter module 446 may present an indication of an artificial sensory experience at least partly based on experimental data. Experimental data may include any data from an experiment, such as a clinical trial. The experiment may be an experiment including an individual and/or a group of people. In one embodiment, experimental data indication presenter module 446 may present an indication of a virtual world suitable for an individual based on a clinical trial involving a group of 1,000 people showing a certain success rate for reducing a phobia, such as fear of heights. In some instances, experimental data indication presenter module 446 may include a computer processor and/or a display device, such as a computer monitor, a mobile phone, and/or a printer.

FIG. 13 illustrates alternative embodiments of the example operational flow 600 of FIG. 6. FIG. 13 illustrates example embodiments where the operation 620 may include at least one additional operation. Additional operations may include an operation 1302, an operation 1304, an operation 1306, and/or an operation 1308.

Operation 1302 illustrates presenting at least one of an indication of an artificial sensory experience or an indication of inhalation therapy at least partly based on a medical reference tool. For example, as shown in FIGS. 1 through 5, reference toot indication presenter module 448 may present an indication of an artificial sensory experience at least partly based on a medical reference tool. A medical reference tool may include a reference book, a reference database, and/or reference software. Some examples of a medical reference book may include a medical dictionary, a medical journal, and/or a book of drug interactions. One example of a reference database may include the National Cancer Center Cancer Image Reference (NCC-CIR) database and/or DynaMed. Some examples of reference software may include Skyscape software for a mobile phone and/or MedAlert. In one embodiment, reference tool indication presenter module 448 may present an indication of an artificial sensory experience based on a reference database, such as a database including data from a clinical trial. In some instances, reference toot indication presenter module 448 may include a computer processor and/or a display device, such as a mobile phone, a printer, and/or a computer monitor.

Operation 1304 illustrates presenting the indication to at least one output device. For example, as shown in FIGS. 1 through 5, output device presenter module 450 may present to at least one output device. In one example, output device presenter module 450 may present an indication of a combination prescription medication and an artificial sensory experience therapy to an output device 130, such as a printer and/or monitor at a health clinic. An output device may include any hardware device configured for receiving computer output. Some examples of an output device may include a printer, a monitor, a mobile phone, a speaker, and/or a visual display unit. The output device 130 may be used by individual 134. In some instances, output device presenter module 450 may include a computer processor.

Further, operation 1306 illustrates presenting the indication to at least one user interface. For example, as shown in FIGS. 1 through 5, user interface presenter module 452 may present to at least one user interface. In one embodiment, user interface presenter module 452 may present to a touchscreen device. A user interface may include means by which an individual may interact with a system. Some examples of a user interface may include a touchscreen, a graphical user interface, a tactile interface, and/or a live user interface. In some instances, user interface presenter module 452 may include a computer processor.

Further, operation 1308 illustrates presenting the indication to at least one mobile device. For example, as shown in FIGS. 1 through 5, mobile device presenter module 454 may present to at least one mobile device. In one embodiment, mobile device presenter module 454 may present to a mobile phone. A mobile device may include a portable computing device and may have wireless connection capability. Some examples of a mobile device may include a laptop or notebook computer, a personal digital assistant (PDA), an ipod, a smartphone, an Enterprise digital assistant (EDA), and/or a pager. In some instances, mobile device presenter module 454 may include a computer processor.

Figure 14:
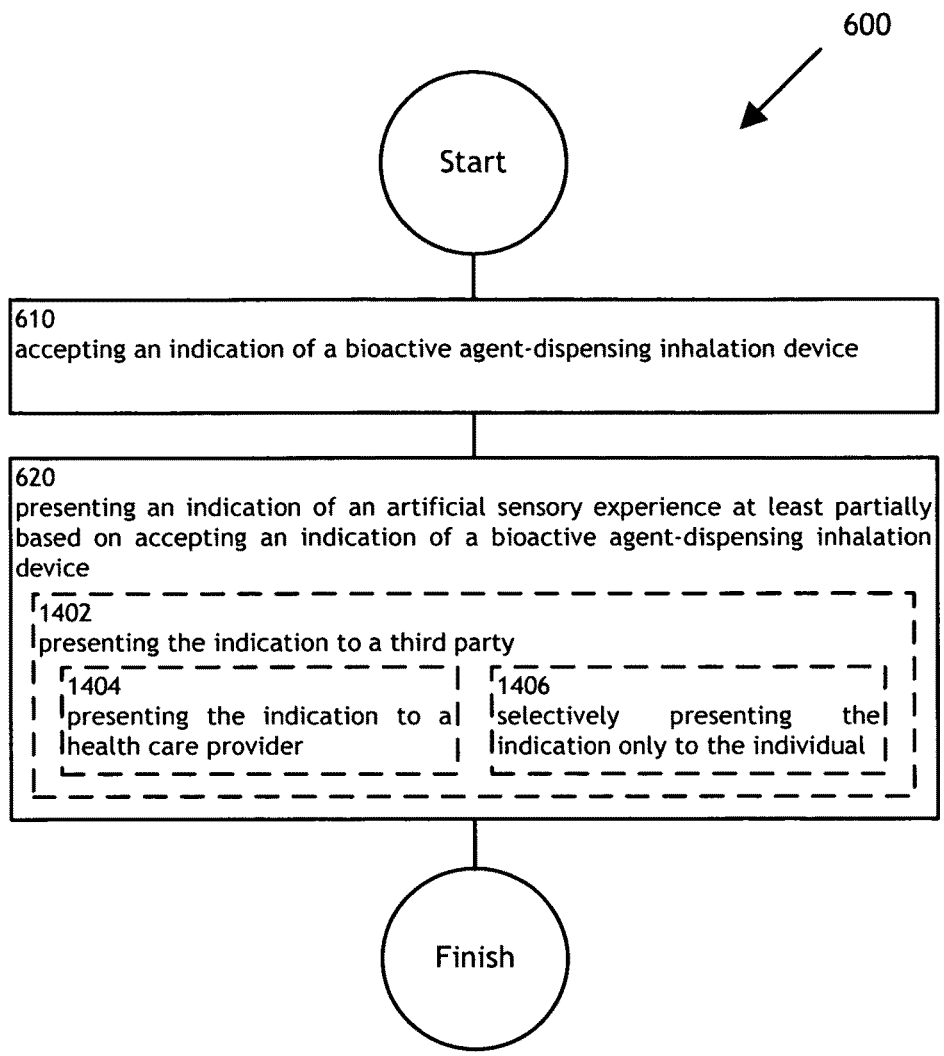
FIG. 14 illustrates an alternative embodiment of the operational flow, of FIG. 6.

FIG. 14 illustrates alternative embodiments of the example operational flow 600 of FIG. 6. FIG. 14 illustrates example embodiments where operation 620 may include at least one additional operation. Additional operations may include operation 1402, operation 1404, and/or operation 1406.

Operation 1402 illustrates presenting the indication to at least one third party. For example, as shown in FIGS. 1 through 5, third party presenter module 456 may present to an individual's physician. A third party may include a party that is an independent party, person, and/or entity. Some examples of a third party may include a physician, a medical database, a hospital, a law enforcement agency, and/or a pharmacy. In one embodiment, third party presenter module 456 may present an indication to an insurance company. Another example of reporting to a third party may include creating displays and reports for aggregating data from therapy results, further discussed in Bair et al., U.S. Pat. No. 6,067,523, which is incorporated herein by reference. In some instances, third party presenter module 456 may include a computer processor and/or a communications device, such as a monitor and network link.

Further, operation 1404 illustrates presenting the indication to at least one health care provider. For example, as shown in FIGS. 1 through 5, health care provider presenter module 458 may present to a health care provider. A health care provider may include a pharmacy, a pharmaceutical company, a medical device company, a research institution, a computer software and/or computer hardware company, a website, a nurse and/or a physician. In one embodiment, health care provider presenter module 458 may present to a physician a prescribed combination artificial sensory experience and bioactive agent therapy via a secured website. In some instances, health care provider presenter module 458 may include a computer processor.

Further, operation 1406 illustrates selectively presenting the indication only to the individual. For example, as shown in FIGS. 1 through 5, selective presenter module 460 may selectively present only to the individual. Selective presenting may include limiting and/or blocking access of an individual's compliance results and/or a prescribed therapy, such as a prescribed artificial sensory experience and/or bioactive agent to a specific party. For example, selective presenter module 460 may present only to individual 134 and may keep results of a certain combination therapy confidential. In one embodiment, an encryption key may be employed to protect selected information. In an additional example, selective presenter module 460 may report only to a law enforcement agency and/or representative, such as a probation officer, and not to individual 134. In some instances, selective presenter module 460 may include a computer processor.

Figure 15:
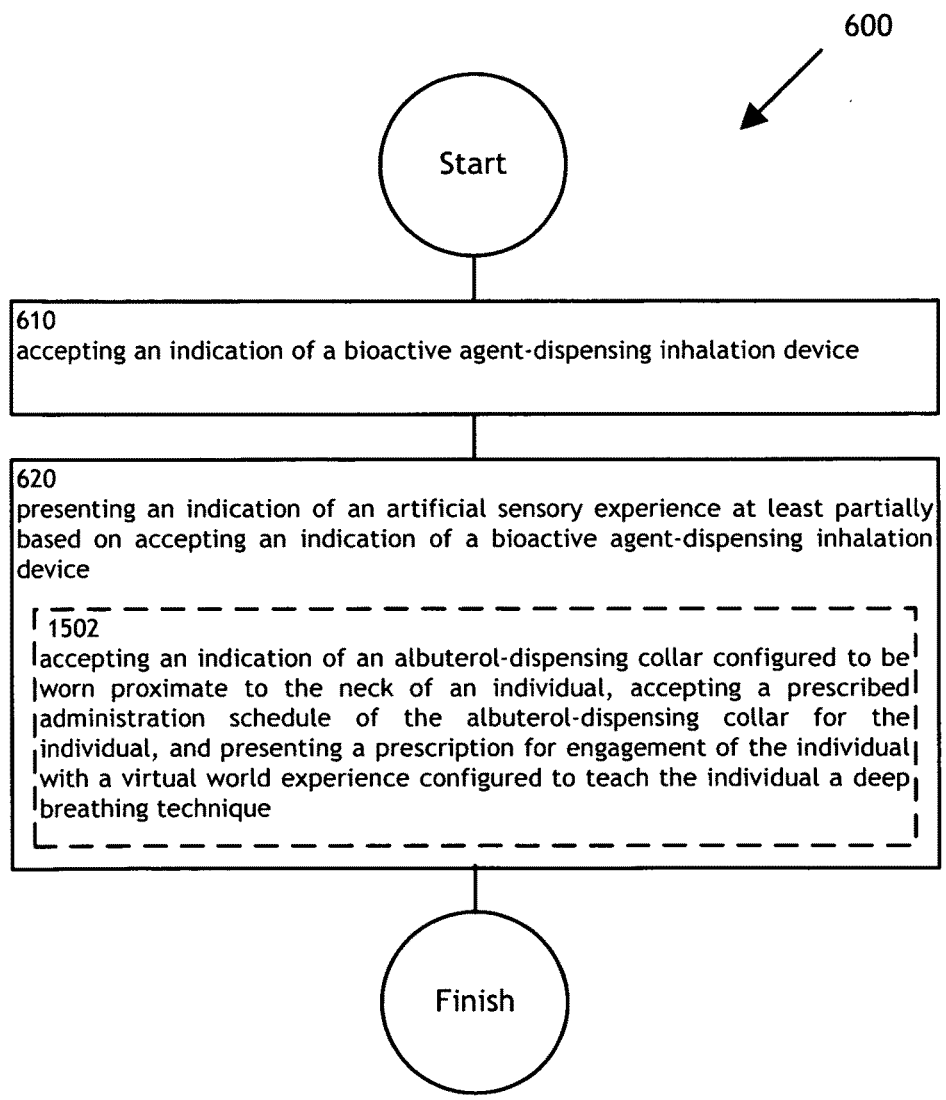
FIG. 15 illustrates an alternative embodiment of the operational flow of FIG. 6.

FIG. 15 illustrates alternative embodiments of the example operational flow 600 of FIG. 6. FIG. 15 illustrates example embodiments where the operation 620 may include at least one additional operation. Additional operations may include an operation 1502.

Operation 1502 illustrates accepting an indication of an individual's asthma, presenting a prescribed administration schedule of an albuterol-dispensing collar therapy for the individual, and presenting a prescription for engagement of the individual with a virtual world experience configured to teach the individual a deep breathing technique. For example, as shown in FIGS. 1 through 5, accepter module 102 and/or presenter module 104 may accept an indication of an albuterol-dispensing collar configured to be worn proximate to the neck of an individual, accept a prescribed administration schedule of the albuterol-dispensing collar for the individual, and present a prescription for engagement of the individual with a virtual world experience configured to teach the individual a deep breathing technique. In some instances, accepter module 102 and/or presenter module 104 may include a computer processor.

Figure 16:
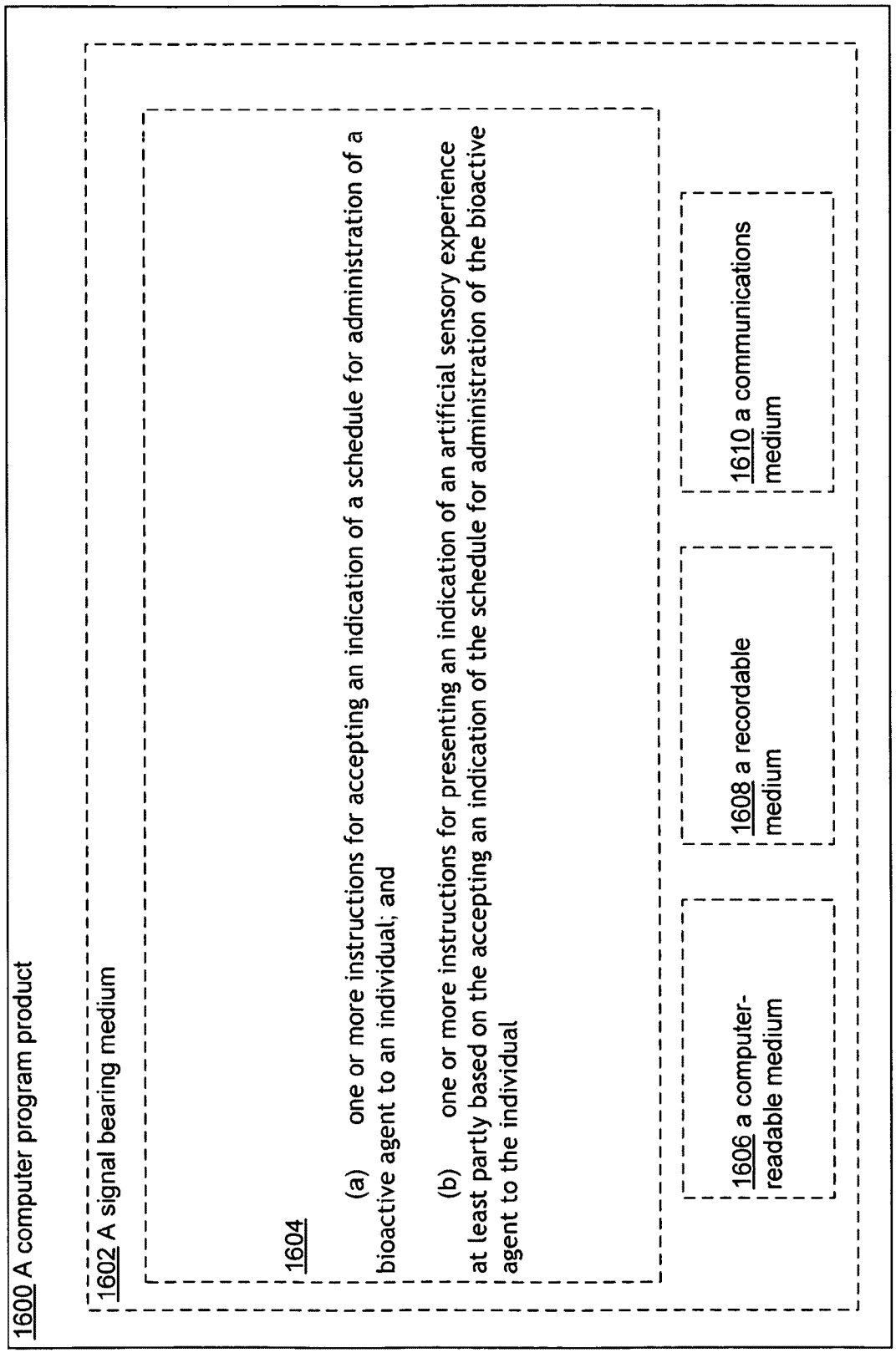
FIG. 16 illustrates a computer program product related to combining an inhaled bioactive agent and an artificial sensory experience.

FIG. 16 illustrates a partial view of an example computer program product 1600 that includes a computer program 1604 for executing a computer process on a computing device. An embodiment of the example computer program product 1600 is provided using a signal-bearing medium bearing 1602, and may include one or more instructions for accepting an indication of at least one health-related condition and one or more instructions for presenting an indication of at least one artificial sensory experience and an indication of at least one inhalation therapy at least partially based on the accepting at least one indication of a health-related condition. The one or more instructions may be, for example, computer executable and/or logic-implemented instructions. In one implementation, the signal-bearing medium 1602 may include a computer-readable medium 1606. In one implementation, the signal bearing medium 1602 may include a recordable medium 1608. In one implementation, the signal bearing medium 1602 may include a communications medium 1610.

Figure 17:
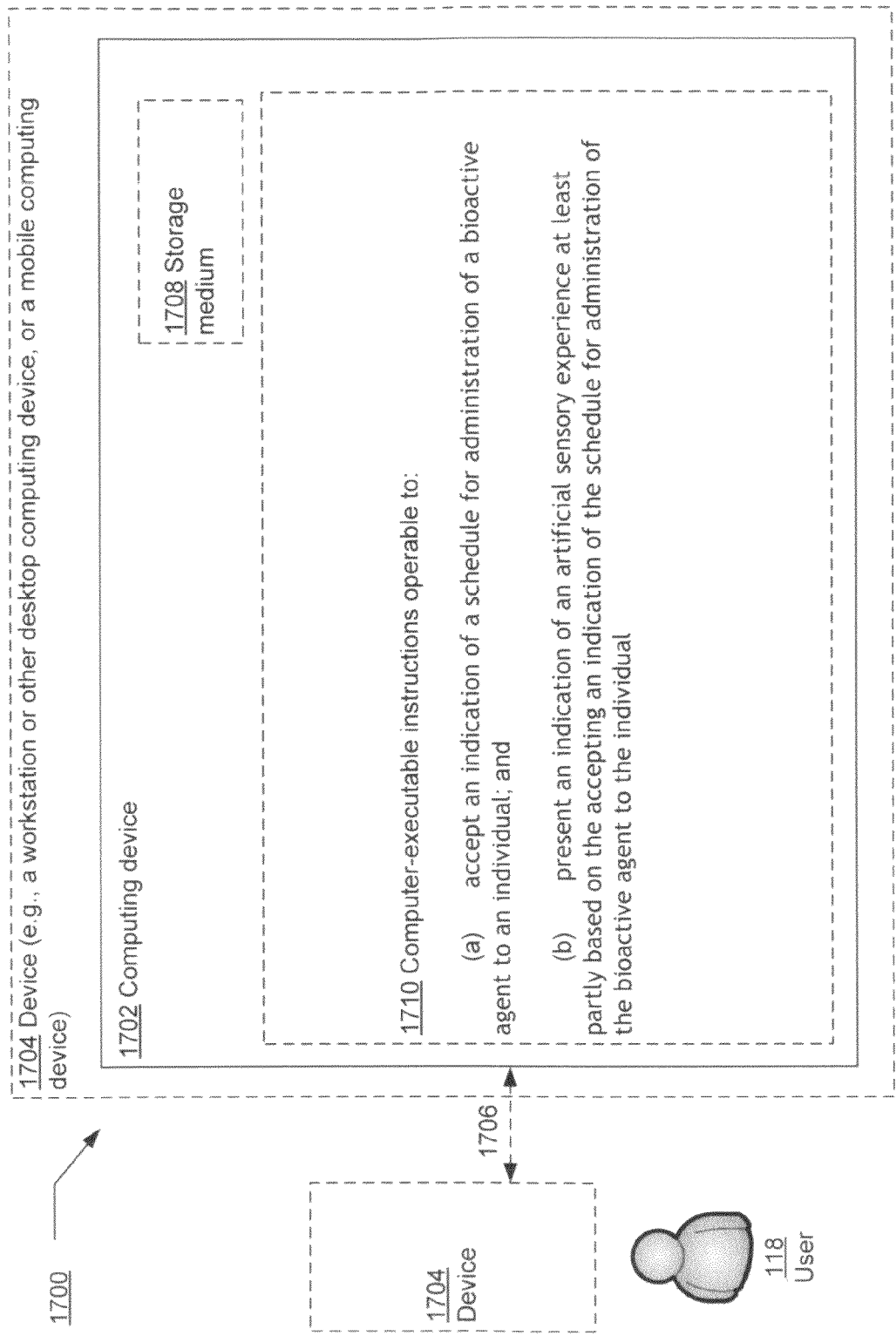
FIG. 17 illustrates a system related to combining an inhaled bioactive agent and an artificial sensory experience.

FIG. 17 illustrates an example system 1700 in which embodiments may be implemented. The system 1700 includes a computing system environment. The system 1700 also illustrates the user 118 using a device 1704, which is optionally shown as being in communication with a computing device 1702 by way of an optional coupling 1706. The optional coupling 1706 may represent a local, wide-area, or peer-to-peer network, or may represent a bus that is internal to a computing device (e.g., in example embodiments in which the computing device 1702 is contained in whole or in part within the device 1704). A storage medium 1708 may be any computer storage media.

The computing device 1702 includes computer-executable instructions 1710 that when executed on the computing device 1702 cause the computing device 1702 to accept an indication of a schedule for administration of a bioactive agent to an individual and present an indication of an artificial sensory experience at least partly based on the accepting an indication of the schedule for administration of the bioactive agent to the individual. As referenced above and as shown in FIG. 17, in some examples, the computing device 1702 may optionally be contained in whole or in part within the device 1704.

In FIG. 17, then, the system 1700 includes at least one computing device (e.g., 1702 and/or 1704). The computer-executable instructions 1710 may be executed on one or more of the at least one computing device. For example, the computing device 1702 may implement the computer-executable instructions 1710 and output a result to (and/or receive data from) the computing device 1704. Since the computing device 1702 may be wholly or partially contained within the computing device 1704, the device 1704 also may be said to execute some or all of the computer-executable instructions 1710, in order to be caused to perform or implement, for example, various ones of the techniques described herein, or other techniques.

The device 1704 may include, for example, a portable computing device, workstation, or desktop computing device. In another example embodiment, the computing device 1702 is operable to communicate with the device 1704 associated with the user 118 to receive information about the input from the user 118 for performing data access and data processing and presenting an output of the user-health test function at least partly based on the user data.

Figure 18:
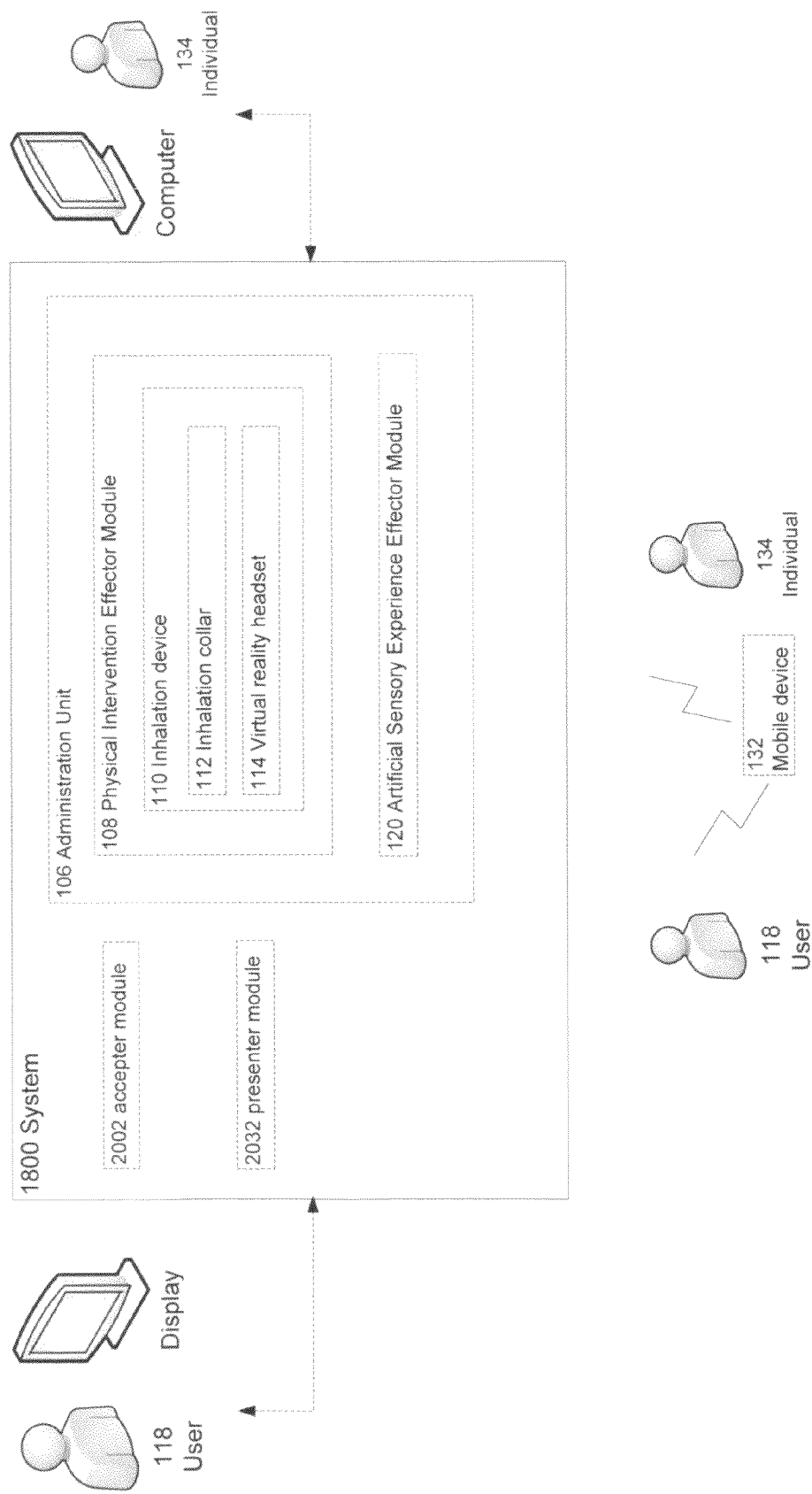
FIG. 18 illustrates an exemplary environment in which one or more technologies may be implemented.

FIG. 18 illustrates system 1800 for accepting an indication of an individual's compliance with an artificial sensory experience and/or presenting an indication of an inhalation device-dispensed bioactive agent at least partially based on the indication of the individual's compliance with the artificial sensory experience. System 1800 may include accepter module 2002, presenter module 2032, and/or administration unit 106. Administration unit 106 may include physical intervention effector module 108 and/or artificial sensory experience effector module 120. Physical intervention effector module 108 may include inhalation device 110. Inhalation device 110 may include inhalation collar 112 and/or virtual reality headset 114. Additionally, system 1800 may include mobile device 132.

Figure 19:
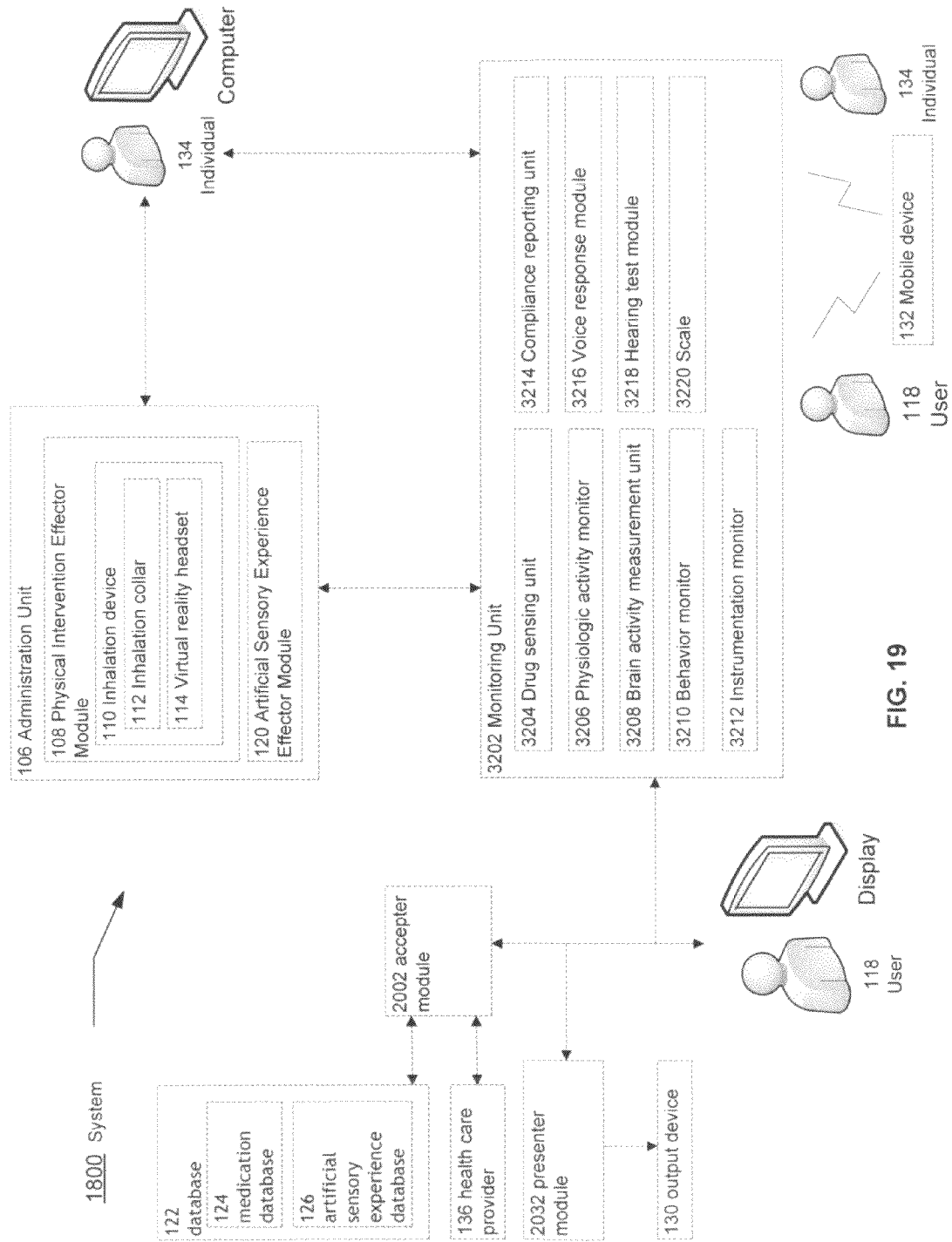
FIG. 19 illustrates an exemplary environment in which one or more technologies may be implemented.

FIG. 19 illustrates system 1800 for accepting an indication of an individual's compliance with an artificial sensory experience and/or presenting an indication of an inhalation device-dispensed bioactive agent at least partially based on the indication of the individual's compliance with the artificial sensory experience. System 1800 may include accepter module 2002, presenter module 2032, accepter module 102, administration unit 106, and/or monitoring unit 3202. Accepter module 2002 may receive and/or transmit information and/or data to and/or from user 118, database 122, output device 130, and/or health care provider 136. A user may include user 118, individual 134, health care provider 136, a patient, and/or another affected person or entity. Database 122 may include medication database 124 and/or artificial sensory experience database 126. Monitoring unit 3202 may monitor individual 134 and may include drug sensing unit 3204, physiologic activity monitor 3206, brain activity measurement unit 3208, behavior monitor 3210, instrumentation monitor 3212, compliance reporting unit 3214, voice response module 3216, hearing test module 3218, and/or scale 3220. Administration unit 106 may include physical intervention effector module 108 and/or artificial sensory experience effector module 120. Physical intervention effector module 108 may include inhalation device 110. Inhalation device 110 may include inhalation collar 112 and/or virtual reality headset 114. Additionally, mobile device 132 may communicate with accepter module 2002, presenter module 2032, healthcare provider 136, user 118, individual 134, monitoring unit 3202, and/or administration unit 106.

Figure 20:
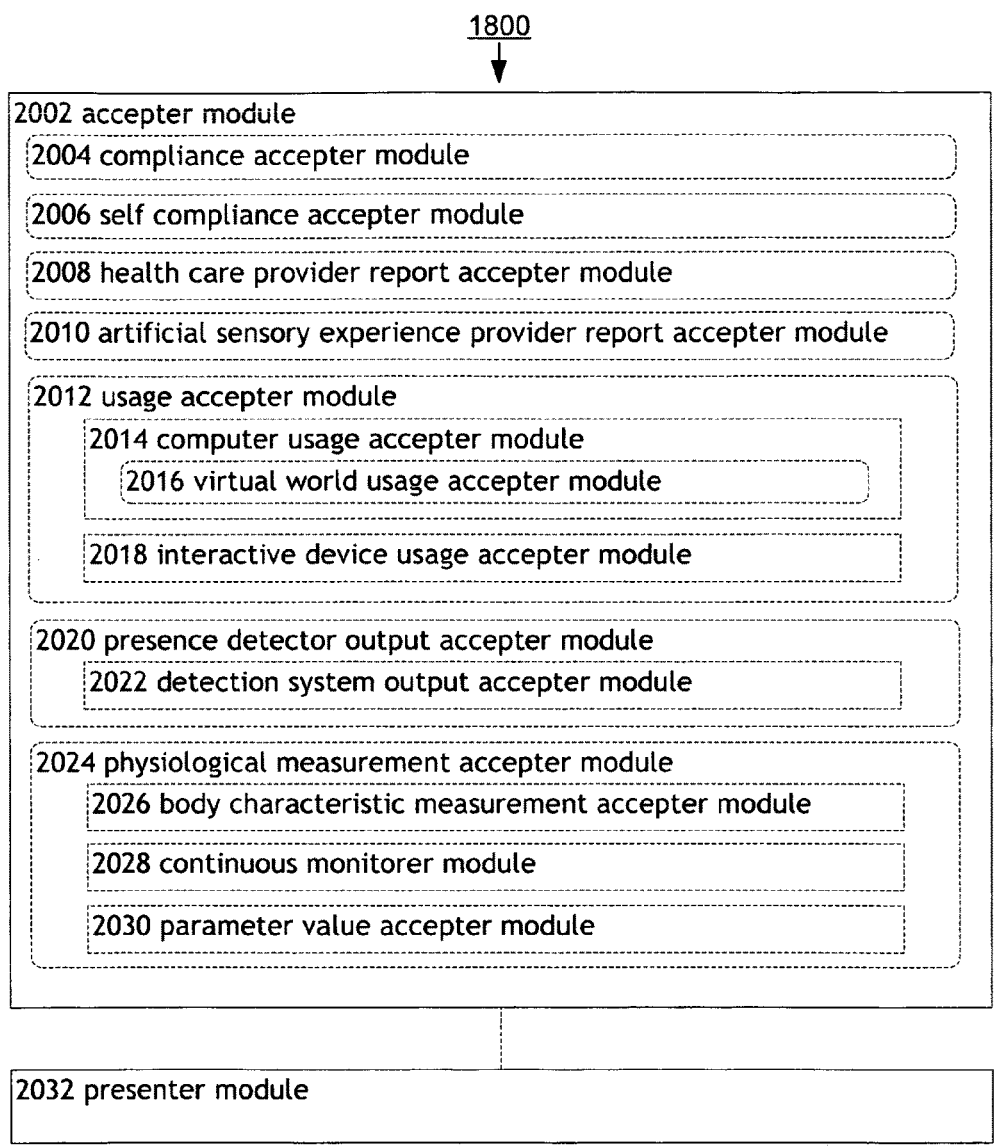
FIG. 20 illustrates an exemplary environment in which one or more technologies may be implemented.

FIG. 20 further illustrates system 1800 including accepter module 2002 and/or presenter module 2032. Accepter module 2002 may include compliance accepter module 2004, self compliance accepter module 2006, health care provider report accepter module 2008, artificial sensory experience provider report accepter module 2010, usage accepter module 2012, presence detector output accepter module 2020, and/or physiological measurement accepter module 2024. Usage accepter module 2012 may include computer usage accepter module 2014 and/or interactive device usage accepter module 2018. Computer usage accepter module 2014 may include virtual world usage accepter module 2016. Presence detector output accepter module 2020 may include detection system output accepter module 2022. Physiological measurement accepter module 2024 may include body characteristic measurement accepter module 2026, continuous monitorer module 2028, and/or parameter value accepter module 2030.

Figure 21:
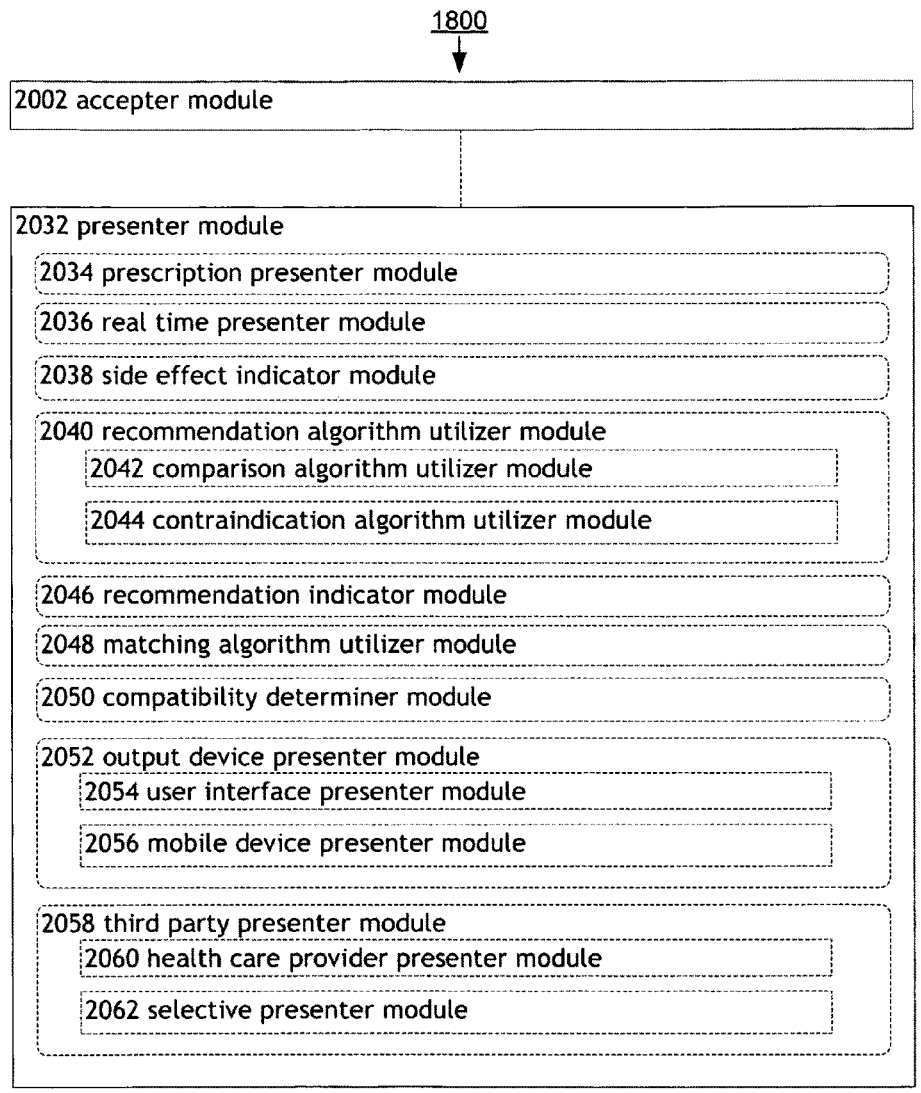
FIG. 21 illustrates an exemplary environment in which one or more technologies may be implemented.

FIG. 21 further illustrates system 1800 including accepter module 2002 and/or presenter module 2032. Presenter module 2032 may include prescription presenter module 2034, real time presenter module 2036, side effect indicator module 2038, recommendation algorithm utilizer module 2040, recommendation indicator module 2046, matching algorithm utilizer module 2048, compatibility determiner module 2050, output device presenter module 2052, and/or third party presenter module 2058. Recommendation algorithm utilizer module 2040 may include comparison algorithm utilizer module 2042 and/or contraindication algorithm utilizer module 2044. Output device presenter module 2052 may include user interface presenter module 2054 and/or mobile device presenter module 2056. Third party presenter module 2058 may include health care provider presenter module 2060 and/or selective presenter module 2062.

System 1800 generally represents instrumentality for accepting an indication of an individual's compliance with an artificial sensory experience and presenting an indication of an inhalation device-dispensed bioactive agent at least partially based on the indication of the individual's compliance with the artificial sensory experience. The operations of accepting an indication of an individual's compliance with an artificial sensory experience and presenting an indication of an inhalation device-dispensed bioactive agent at least partially based on the indication of the individual's compliance with the artificial sensory experience may be accomplished electronically, such as with a set of interconnected electrical components, an integrated circuit, and/or a computer processor.

FIG. 22 illustrates an operational flow 2200 representing example operations related to accepting an indication of an individual's compliance with an artificial sensory experience and presenting an indication of an inhalation device-dispensed bioactive agent at least partially based on the indication of the individual's compliance with the artificial sensory experience. In FIG. 22 and in following figures that include various examples of operational flows, discussion and explanation may be provided with respect to the above-described examples of FIGS. 18 through 21, and/or with respect to other examples and contexts. However, it should be understood that the operational flows may be executed in a number of other environments and contexts, and/or in modified versions of FIGS. 18 through 21. Also, although the various operational flows are presented in the sequence(s) illustrated, it should be understood that the various operations may be performed in other orders than those which are illustrated, or may be performed concurrently.

After a start operation, the operational flow 2200 moves to an operation 2210. Operation 2210 depicts accepting an indication of an individual's compliance with an artificial sensory experience. For example, as shown in FIGS. 18 through 21, accepter module 2002 may accept an indication of an individual's compliance with an artificial sensory experience. In an embodiment, accepter module 2002 may accept a computer usage log for a virtual world account for an individual indicating the individual was engaged with the virtual world for a prescribed amount of time. In this embodiment, the virtual world may be a prescribed artificial sensory experience for the individual where a computer log may indicate an individual's usage of the virtual world and further indicate compliance with the prescription artificial sensory experience. In some instances, accepter module 2002 may include a computer processor.

Then, operation 2220 depicts presenting an indication of an inhalation device-dispensed bioactive agent at least partially based on the indication of the individual's compliance with the artificial sensory experience. For example, as shown in FIGS. 18 through 21, presenter module 2032 may present an indication of an inhalation device-dispensed bioactive agent based on the indication of the individual's compliance with the artificial sensory experience, such as a prescribed artificial sensory experience. In one example, presenter module 2032 may present an indication of a bronchodilator, such as albuterol, based on an indication of an RFID tag configured to indicate compliance with a physician's prescription for a virtual world. In this example, the indication of the RFID tag may indicate, for example, a certain time length that the individual has experienced the virtual world and may help specifiy an optimized time at which the bioactive agent may be dispensed. In some instances, presenter module 2032 may include a computer processor, a computer printer, a mobile device, and/or a computer monitor.

Figure 23:
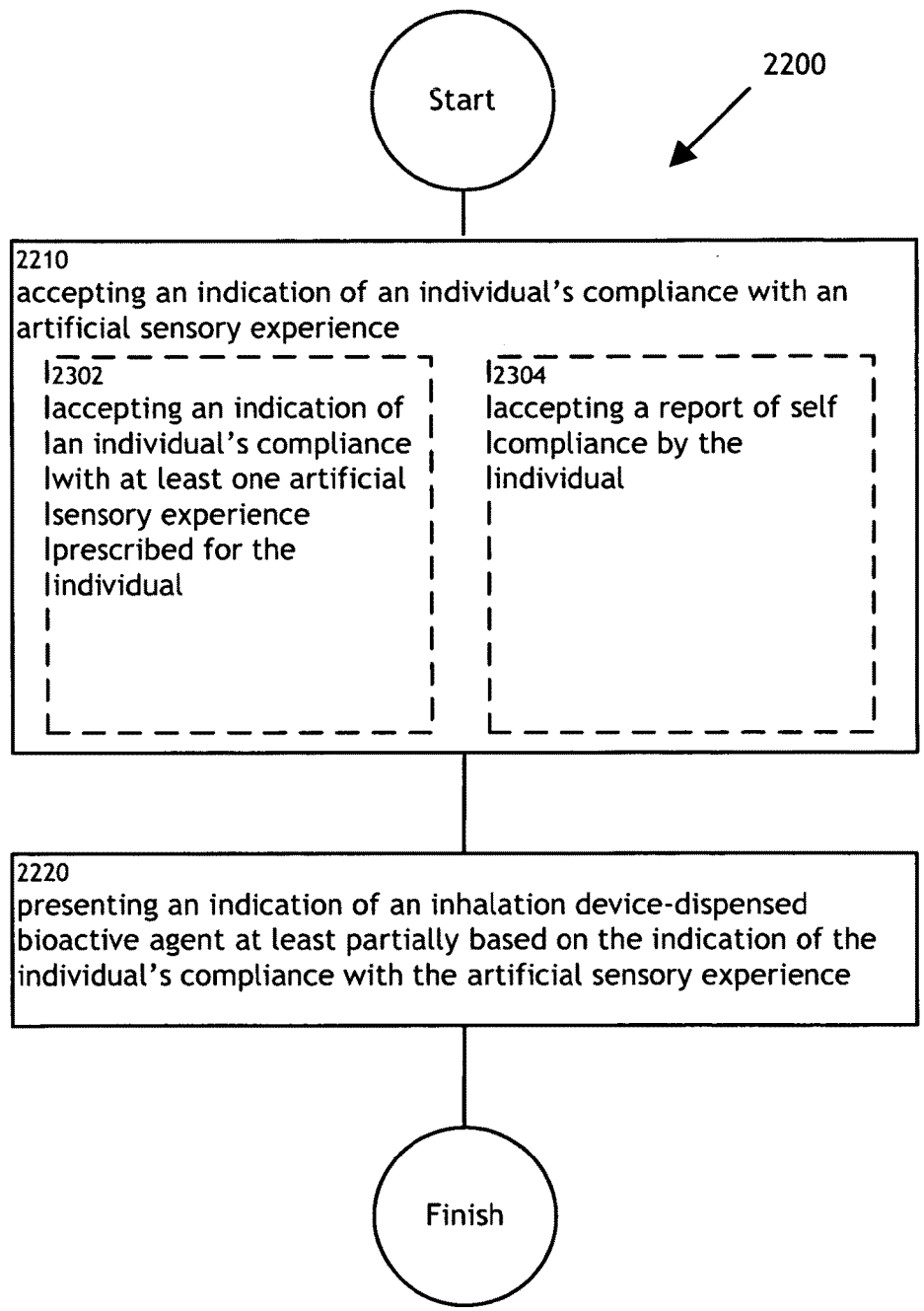
FIG. 23 illustrates an alternative embodiment of the operational flow of FIG. 22.

FIG. 23 illustrates alternative embodiments of the example operational flow 2200 of FIG. 22. FIG. 23 illustrates example embodiments where operation 2210 may include at least one additional operation. Additional operations may include operation 2302, and/or operation 2304.

Operation 2302 illustrates accepting an indication of an individual's compliance with at least one artificial sensory experience prescribed for the individual. For example, as shown in FIGS. 18 through 21, compliance accepter module 2004 may accept an indication of an individual's compliance with at least one artificial sensory experience prescribed for the individual. In one embodiment, compliance accepter module 2004 may accept an indication of an individual's compliance with a virtual world prescribed for the individual. Some examples of an individual's compliance may include a computer entry by the individual and/or a computer entry by a health care provider. Additionally, a prescribed artificial sensory experience may include a prescription from a health care provider, such as a physician, a psychiatrist, and/or a nurse practitioner. In some instances, compliance accepter module 2004 may include a computer processor.

Operation 2304 illustrates accepting a report of self compliance by the individual. For example, as shown in FIGS. 18 through 21, self compliance accepter module 2006 may present an indication of a bioactive agent based on the indication of the individual's compliance with the artificial sensory experience, such as a prescribed artificial sensory experience. In one example, self compliance accepter module 2006 may present an indication of an antianxiety medication, such as Xanax, based on an indication of an RFID tag configured to indicate compliance with a physician's prescription for a virtual world. An additional example may include an individual entering a compliance status into a computer. In some instances, self compliance accepter module 2006 may include a computer processor.

FIG. 24 illustrates alternative embodiments of the example operational flow 2200 of FIG. 22. FIG. 24 illustrates example embodiments where operation 2210 may include at least one additional operation. Additional operations may include operation 2402, and/or operation 2404.

Operation 2402 illustrates accepting a report of the individual's compliance from a health care provider. For example, as shown in FIGS. 18 through 21, health care provider report accepter module 2008 may accept a report of the individual's compliance from a health care provider. In one embodiment, health care provider report accepter module 2008 may accept a report from an individual's psychiatrist of the individual's compliance with a prescription for an online tutorial. In this embodiment, the health care provider may report compliance, for example, by inputting an indication of compliance into a program and/or entering it into a computer. Other examples of health care provider reporting of an individual's compliance may include entering an indication of compliance on a website, and/or using a telephone prompt system to enter an indication of compliance at a remote location. In some instances, health care provider report accepter module 2008 may include a computer processor.

Operation 2404 illustrates accepting a report of the individual's compliance from an artificial sensory experience provider. For example, as shown in FIGS. 18 through 21, artificial sensory experience provider report accepter module 2010 may accept a report of the individual's compliance from an artificial sensory experience provider. In one embodiment, artificial sensory experience provider report accepter module 2010 may accept a report of an individual's compliance from a software company, such as Blizzard Entertainment. In this embodiment, the software company may mine compliance data from an individual's activity in an artificial sensory experience, such as World of Warcraft, created by the software company and send the information to artificial sensory experience provider report accepter module 2010. In some instances, artificial sensory experience provider report accepter module 2010 may include a computer processor and/or instrumentation configured to receive data, such as a data modem.

FIG. 25 illustrates alternative embodiments of the example operational flow 2200 of FIG. 22. FIG. 25 illustrates example embodiments where operation 2210 may include at least one additional operation. Additional operations may include operation 2502, operation 2504, operation 2506, and/or operation 2508.

Operation 2502 illustrates accepting an indication of artificial sensory experience usage by the individual. For example, as shown in FIGS. 18 through 21, usage accepter module 2012 may accept an indication of artificial sensory experience usage by the individual. In one embodiment, usage accepter module 2012 may accept an indication of usage of a virtual world, such as World of Warcraft, by the individual. One example of artificial sensory experience usage may include an amount of time the individual is engaged in the artificial sensory experience. Another example of measuring artificial sensory experience usage may include accepting a certain score, where each score may be correlated with progress in the artificial sensory by the individual. Further discussion regarding an example of accepting an indication of artificial sensory usage and feedback may be found in Jung et al., U.S. Patent Publication No. 2007/0112624, which is incorporated herein by reference. In some instances, usage accepter module 2012 may include a computer processor.

Further, operation 2504 illustrates accepting an indication of computer usage. For example, as shown in FIGS. 18 through 21, computer usage accepter module 2014 may accept an indication of computer usage. In one embodiment, computer usage accepter module 2014 may accept an indication of a computer's usage by accessing a certain individual's account log. In another example, computer usage accepter module 2014 may accept user interaction with a computer generated virtual reality environment, one example being further discussed in Elkind, U.S. Pat. No. 6,149,586, which is incorporated herein by reference. In some instances, computer usage accepter module 2014 may include a computer processor.

Further, operation 2506 illustrates accepting an indication of at least one of virtual world usage or a computer activity log. For example, as shown in FIGS. 18 through 21, virtual world usage accepter module 2016 may accept an indication of at least one of virtual world usage and/or a computer activity log. An indication of virtual world usage may include a report, such as a self report and/or a computer generated report showing, for example, an amount of time spent by an individual complying with an artificial sensory experience prescription. A computer activity log may include any practice where sequential data may be recorded. Some examples of a computer activity log may include a web counter, a server log, and/or using logging related software, such as Multitail and/or Pantheios. In one embodiment, virtual world usage accepter module 2016 may accept a computer activity log from a computer program, such as Pantheios, indicating usage by a specific individual. In some instances, virtual world usage accepter module 2016 may include a computer processor.

Further, operation 2508 illustrates accepting an indication of interactive device usage. For example, as shown in FIGS. 18 through 21, interactive device usage accepter module 2018 may accept an indication of usage of an interactive device. Some examples of an interactive device may include a user interface, an interactive whiteboard, a flight simulator, and/or a wired glove. In one embodiment, interactive device usage accepter module 2018 may accept an indication of usage of a virtual world coupled with a wired glove. Other examples of an interactive device may include a virtual reality exercise machine and a hand-held computer interactive device respectively found in Jarvik, U.S. Pat. No. 5,577,981, and Daniel, U.S. Pat. No. 7,161,579, each of which is incorporated herein by reference. In some instances, interactive device usage accepter module 2018 may include a computer processor.

Figure 26:
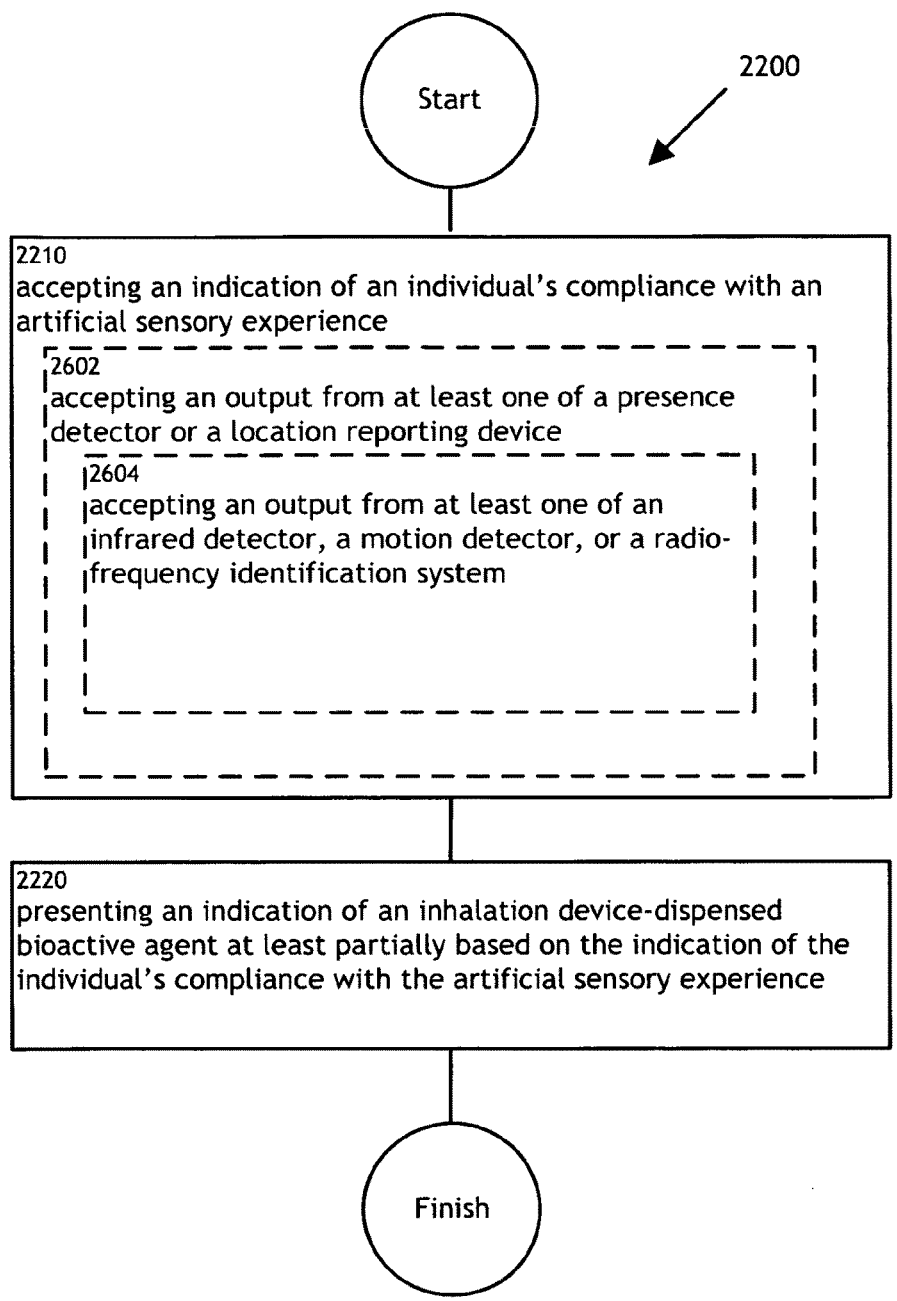
FIG. 26 illustrates an alternative embodiment of the operational flow of FIG. 22.

FIG. 26 illustrates alternative embodiments of the example operational flow 2200 of FIG. 22. FIG. 26 illustrates example embodiments where operation 2210 may include at least one additional operation. Additional operations may include operation 2602, and/or operation 2604.

Operation 2602 illustrates accepting an output from at least one of a presence detector or a location reporting device. For example, as shown in FIGS. 18 through 21, presence detector output accepter module 2020 may accept an output from at least one of a presence detector or a location reporting device. In one embodiment, presence detector output accepter module 2020 may accept an output from a motion detector. Accepting an output may include, for example, accepting a signal, such as an electrical and/or optical signal. A presence detector and/or a location reporting device may include a device configured for detection or location reporting of an individual, for example using sound, heat, and/or motion. Some examples of a presence detector may include a safety laser scanner, available from OMRON Corporation, Kyoto, Japan, and/or a speech presence detector, such as discussed in Taylor et al., U.S. Pat. No. 5,822,726, which is incorporated herein by reference. Another example of a presence detector may include a camera coupled to a motion sensor, such as the VIR-101 infrared motion detector w/camera available from Security Labs®, Noblesville, Ind. Other example of a presence detector may include a pressure sensor and/or a microphone. In some instances, presence detector output accepter module 2020 may include a computer processor.

Further, operation 2604 illustrates accepting an output from at least one of an infrared detector, a motion detector, or a radio-frequency identification system. For example, as shown in FIGS. 18 through 21, detection system output accepter module 2022 may accept an output from a radio-frequency identification (RFID) tag. A radio frequency identification system may include a system utilizing radio frequency signals to identify an object or a person, such as in the case of using an RFID tag. A RFID tag may include on object which may be applied to or included in an object, where the RFID tag utilizes radio waves for the purpose of identification. A RFID tag may include an integrated circuit for storing and/or processing information along with an antenna for receiving and transmitting a signal. In one embodiment, detection system output accepter module 2022 may accept an output from a RFID tag on an individual's person, where the RFID tag may have a limited range for signal transmission/reception. In this embodiment, proximity of the RFID tag to detection system output accepter module 2022 combined with the limited signal transmission/reception range may indicate a likelihood that an individual may be engaged in an artificial sensory experience, such as logging on to a virtual world. In another embodiment, detection system output accepter module 2022 may accept an output from an infrared detector that is placed proximate to a computer where an individual engages in a prescribed artificial sensory experience. In this embodiment, the infrared detector may detect the individual, for example by infrared light radiating from the individual, while engaging in the prescribed artificial sensory experience. Additionally, detection system output accepter module 2022 may be coupled to, for example, a logging and/or recording device for recording the amount of time and/or whether the individual complied with a prescription for an artificial sensory experience. In some instances, detection system output accepter module 2022 may include a computer processor and/or instrumentation, such as a passive infrared sensor. One example of a passive infrared sensor may be found in Owers, U.S. Pat. No. 4,734,585, which is incorporated herein by reference.

FIG. 27 illustrates alternative embodiments of the example operational flow 2200 of FIG. 22. FIG. 27 illustrates example embodiments where operation 2210 may include at least one additional operation. Additional operations may include operation 2702, operation 2704, operation 2706, and/or operation 2708.

Operation 2702 illustrates accepting an indication of a physiological measurement. For example, as shown in FIGS. 18 through 21, physiological measurement accepter module 2024 may accept an indication of a physiological measurement. In one embodiment, physiological measurement accepter module 2024 may accept an indication of a heart rate from a physiological measurement device, such as the device discussed in Chang, U.S. Patent Publication No. 2007/0123783, which is incorporated herein by reference. A physiological measurement may include a measurement of the mechanical, physical, and/or biochemical functions of the body. Some examples of a physiological measurement may include body weight, blood pressure, heart rate, blood oxygen level, and/or body temperature. In some instances, physiological measurement accepter module 2024 may include a computer processor.

Further, operation 2704 illustrates accepting an indication of at least one of a respiratory rate, body weight, body mass index number, heart rate, blood oxygen level, or blood pressure proximate to administration of the bioactive agent. For example, as shown in FIGS. 18 through 21, body characteristic measurement accepter module 2026 may accept an indication of at least one of a respiratory rate, body weight, body mass index number, heart rate, blood oxygen level, or blood pressure proximate to administration of the bioactive agent. In one embodiment, body characteristic measurement accepter module 2026 may accept an indication of a respiratory rate from a physiological measurement device. A respiratory rate may include the number of breaths taken per minute. Accepting an indication of body weight and/or a body mass index number may include accepting information from a scale and/or a computing device. In one embodiment, body characteristic measurement accepter module 2026 may accept a body weight of an individual experiencing a Wii Fitness game while being administered an inhaled weight loss medication by using a scale 3220 coupled with a computer processor. In the same embodiment, scale 3220 and a computer processor may constantly monitor the body mass index of the individual. Further, accepting an indication of a heart rate may include accepting a measurement of work done by the heart, such as a measurement of beats per unit time and/or a pulse. Accepting an indication of a blood oxygen level may include accepting a measurement from a pulse oximeter and/or a measurement of oxygen saturation directly through a blood sample. Accepting an indication of blood pressure may include accepting a measurement of blood pressure from, for example, a sphygmomanometer, which may be coupled to a computer processor or other monitoring device. Additionally, body characteristic measurement accepter module 2026 may accept a physiological measurement before, during, and/or after an artificial sensory experience and/or bioactive agent administration. In some instances, body characteristic measurement accepter module 2026 may include a computer processor and/or other medical instrumentation, such as that discussed herein.

Further, operation 2706 illustrates continuously monitoring a parameter of a physiological measurement. For example, as shown in FIGS. 18 through 21, continuous monitorer module 2028 may continuously monitor a parameter of a physiological measurement. In one embodiment, continuous monitorer module 2028 may continuously and remotely monitor perspiration data for an individual. Continuous monitoring may include measuring a specified parameter without interruption and/or delay. One example of a system configured for continuously and/or remotely monitoring a medical parameter may be found in Rode et al., U.S. Pat. No. 6,315,719, which is incorporated herein by reference. In some instances, continuous monitorer module 2028 may include a computer processor and/or medical instrumentation, such as that described herein.

Further, operation 2708 illustrates accepting an indication of a current parameter value compared with an expected parameter value. For example, as shown in FIGS. 18 through 21, parameter value accepter module 2030 may accept an indication of a current parameter value compared with an expected parameter value. In one embodiment, parameter value accepter module 2030 may accept an indication of a current blood pressure measurement compared with an expected blood pressure value. By comparing a current parameter with an expected value, efficacy of an artificial sensory experience and/or a bioactive may be determined. For example, if a current blood pressure measurement is higher than an expected blood pressure value, a health care provider may determine that an artificial sensory experience and/or bioactive agent is not efficacious and may prescribe an alternative artificial sensory experience and/or bioactive agent. In some instances, parameter value accepter module 2030 may include a computer processor.

FIG. 28 illustrates alternative embodiments of the example operational flow 2200 of FIG. 22. FIG. 28 illustrates example embodiments where operation 2220 may include at least one additional operation. Additional operations may include operation 2802, operation 2804, and/or operation 2806.

Operation 2802 illustrates presenting an identification of a prescribed inhalation device-dispensed bioactive agent. For example, as shown in FIGS. 18 through 21, prescription presenter module 2034 may present an identification of a prescribed inhalation device-dispensed bioactive agent. In one embodiment, prescription presenter module 2034 may present an identification of a prescribed inhalation device-dispensed bioactive agent to a pharmacy. Additionally, prescription presenter module 2034 may present to other entities, such as a hospital, a physician, a nurse, and/or an insurance company. An additional example of presenting bioactive agent information may be found in Mayaud, U.S. Publication No. 2003/01444884, which is incorporated herein by reference. In some instances, prescription presenter module 2034 may include a computer processor.

Operation 2804 illustrates presenting at least one effect of the inhalation device-dispensed bioactive agent in near real time. For example, as shown in FIGS. 18 through 21, real time presenter module 2036 may present at least one effect of the inhalation device-dispensed bioactive agent in near real time. A near real time event may include the current time of an event plus processing time. In one embodiment, real time presenter module 2036 may present in near real time an effect of a bronchodilator on an individual's respiration rate to a supervising physician. A further example of presenting in real time and/or near real time, including real-time medical alerting, may be found in McGovern, U.S. Pat. No. 6,909,359, which is incorporated herein by reference. In some instances, real time presenter module 2036 may include a computer processor.

Operation 2806 illustrates indicating at least one side effect of the inhalation device-dispensed bioactive agent. For example, as shown in FIGS. 18 through 21, side effect indicator module 2038 may indicate at least one side effect of the inhalation device-dispensed bioactive agent. In one embodiment, side effect indicator module 2038 may indicate a drop in heart rate caused by an inhaled anti anxiety medication. Some examples of side effects may include fever, hypertension, and/or headache, as well as other side effects known in medicine. In some instances, side effect indicator module 2038 may include a computer processor.

FIG. 29 illustrates alternative embodiments of the example operational flow 2200 of FIG. 22. FIG. 29 illustrates example embodiments where operation 2220 may include at least one additional operation. Additional operations may include operation 2902, operation 2904, and/or operation 2906.

Operation 2902 illustrates utilizing an algorithm configured for recommending the inhalation device-dispensed bioactive agent. For example, as shown in FIGS. 18 through 21, recommendation algorithm utilizer module 2040 may utilize an algorithm configured for recommending the inhalation device-dispensed bioactive agent. An algorithm configured for recommending the inhalation device-dispensed bioactive agent may include any computation, formula, statistical survey, and/or look-up table for determining and/or selecting a suitable prescription medication combination. Some examples may include a computer software algorithm, a calculator, a flowchart, and/or a decision tree. In one embodiment, recommendation algorithm utilizer module 2040 may utilize an algorithm that uses an inputted artificial sensory experience and compares the artificial sensory experience with information in a clinical trial database for determining inhalation device-dispensed bioactive agent comparability. In some instances, recommendation algorithm utilizer module 2040 may include a computer processor.

Further, operation 2904 illustrates utilizing an algorithm configured for comparing at least one effect of the inhalation device-dispensed bioactive agent with at least one expected behavior of the individual at one or more times proximate to the individual's use of the artificial sensory experience. For example, as shown in FIGS. 18 through 21, comparison algorithm utilizer module 2042 may utilize an algorithm configured for comparing at least one effect of the inhalation device-dispensed bioactive agent with at least one expected behavior of the individual at one or more times proximate to the individual's use of the artificial sensory experience. In one embodiment, comparison algorithm utilizer module 2042 may utilize a comparison algorithm configured for comparing an inhaled antianxiety medication with a heart rate measurement proximate to an artificial sensory experience configured for reducing a phobia, such as a fear of heights. Such a comparison may indicate a need to modify and/or efficacy of a prescribed artificial sensory experience and/or inhalation device-dispensed bioactive agent. In some instances, comparison algorithm utilizer module 2042 may include a computer processor.

Further, operation 2906 illustrates utilizing an algorithm configured for identifying a contraindication of the inhalation device-dispensed bioactive agent. For example, as shown in FIGS. 18 through 21, contraindication algorithm utilizer module 2044 may utilize an algorithm configured for identifying a contraindication of the inhalation device-dispensed bioactive agent. A contraindication of an inhalation device-dispensed bioactive agent may include giving an indication against the advisability of the bioactive agent. For example, contraindication algorithm utilizer module 2044 may utilize an algorithm that considers an individual's personal medical history and may recommend not prescribing a certain medication. Contraindication algorithm utilizer module 2044 may identify a contraindication of an inhalation device-dispensed bioactive agent for reasons such as an adverse reaction and/or inefficacy. In some instances, contraindication algorithm utilizer module 2044 may include a computer processor.

FIG. 30 illustrates alternative embodiments of the example operational flow 2200 of FIG. 22. FIG. 30 illustrates example embodiments where operation 2220 may include at least one additional operation. Additional operations may include operation 3002, operation 3004, and/or operation 3006.

Operation 3002 illustrates indicating at least one of a recommended dosage or a recommended delivery method. For example, as shown in FIGS. 18 through 21, recommendation indicator module 2046 may indicate at least one of a recommended bioactive agent dosage or a recommended bioactive agent delivery method. In one embodiment, recommendation indicator module 2046 may indicate a recommended bioactive dosage, such as a dosage reduction for an inhaled asthma medication. Recommendation indicator module 2046 may recommend an initial dosage and may also recommend a change in dosage, such as an increased or reduced dosage. One example of reducing a bioactive agent dosage using a controller in an implanted device may be found in Shelton, U.S. Patent Publication No. 2008/0172044, which is incorporated herein by reference. Some examples of bioactive delivery methods may include mucosal administration, parenteral administration (such as intravenous, intramuscular, and/or subcutaneous administration), topical administration such as epicutaneous administration, inhalational administration, transdermal administration, and/or enteral therapy, such as a pill taken orally, or the like. In one instance, recommendation indicator module 2046 may include a computer processor.

Operation 3004 illustrates utilizing an algorithm configured for matching at least one detected physiologic attribute of the individual with a prescription inhalation device-dispensed medication at a time proximate to the individual's use of the artificial sensory experience. For example, as shown in FIGS. 18 through 21, matching algorithm utilizer module 2048 may utilize an algorithm configured for matching at least one detected physiologic attribute of the individual with a prescription inhalation device-dispensed medication at a time proximate to the individual's use of the artificial sensory experience. In one embodiment, matching algorithm utilizer module 2048 may use an algorithm configured for matching a detected physiologic attribute, such as blood pressure, with an inhaled asthma medication at a time proximate to an artificial sensory experience, such as a virtual world configured to reduce a fear of flying. The use of such an algorithm may serve to increase efficacy and compatability of an artificial sensory experience and/or an inhalation device-dispensed bioactive agent. By matching a physiologic attribute with a prescription inhalation device-dispensed medication proximate in time to an artificial sensory experience, a health care provider may more effectively prescribe an inhalation device-dispensed medication because the health care provider may be more likely to determine that the artificial sensory experience may be the cause of the physiologic attribute. In some instances, matching algorithm utilizer module 2048 may include a computer processor.

Operation 3006 illustrates determining a compatibility between the artificial sensory experience and the inhalation device-dispensed bioactive agent using at least one of a medical history, experimental data, or a medical reference book. For example, as shown in FIGS. 18 through 21, compatibility determiner module 2050 may determine compatibility between the artificial sensory experience and the inhalation device-dispensed bioactive agent using at least one of a medical history, experimental data, or a medical reference book. A medical history may include a personal history and/or a family history. A personal medical history may include a list of previous illnesses, symptoms, medicines, treatments, health risk factors, operations, and/or doctor visits associated with at least one individual. A personal and/or a family medical history may include life history and/or social history characteristics such as smoking, drinking, drug use, sexual history, exercise history, eating history, nutraceutical history, or the like. Experimental data may include any data from an experiment, such as a clinical trial. The experiment may be an experiment including an individual and/or a group of people. Some examples of a medical reference book may include a medical dictionary, a medical journal, and/or a book of drug interactions. In one embodiment, compatibility determiner module 2050 may determine a compatability of an inhaled bronchodilator and a virtual world designed to overcome a phobia. In this embodiment, compatibility determiner module 2050 may use, for example, experimental and empirical data including clinical trial results from a group of people previously having used the same combination bronchodilator and virtual world designed to overcome a phobia. In another embodiment, compatibility determiner module 2050 may determine a compatability using an individual's personal medical history including previous artificial sensory experience and inhalation device-dispensed bioactive agent interactions. In some instances, compatibility determiner module 2050 may include a computer processor.

Figure 31:
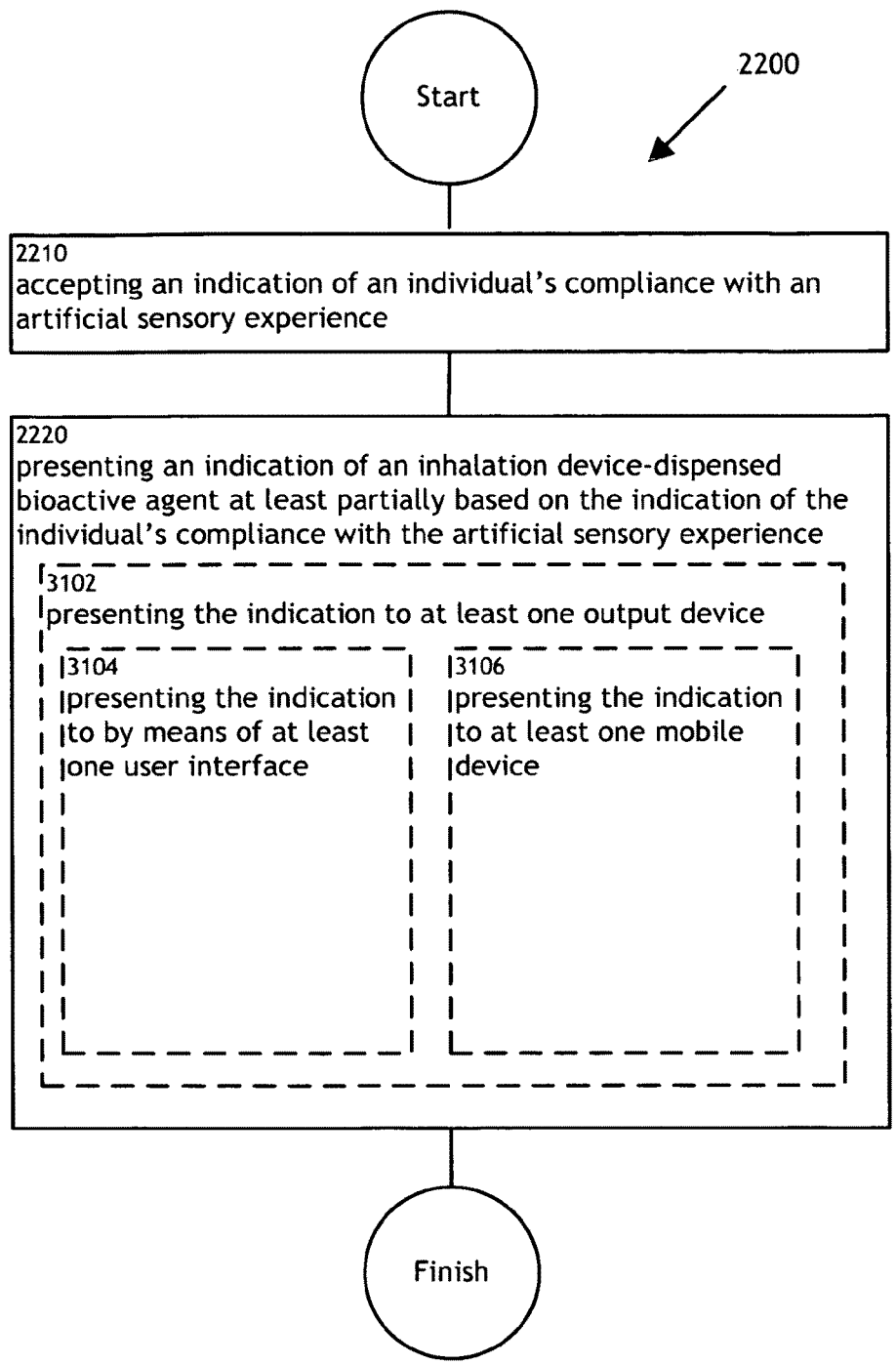
FIG. 31 illustrates an alternative embodiment of the operational flow of FIG. 22.

FIG. 31 illustrates alternative embodiments of the example operational flow 2200 of FIG. 22. FIG. 31 illustrates example embodiments where operation 2220 may include at least one additional operation. Additional operations may include operation 3102, operation 3104, and/or operation 3106.

Operation 3102 illustrates presenting the indication to at least one output device. For example, as shown in FIGS. 18 through 21, output device presenter module 2052 may present to at least one output device. In one example, output device presenter module 2052 may present an indication of a combination prescription medication and an artificial sensory experience therapy to an output device 130, such as a printer and/or monitor at a health clinic. An output device may include any hardware device configured for receiving computer output. Some examples of an output device may include a printer, a monitor, a mobile phone, a speaker, and/or a visual display unit. The output device 130 may be used by individual 134. In some instances, output device presenter module 2052 may include a computer processor.

Further, operation 3104 illustrates presenting the indication by means of at least one user interface. For example, as shown in FIGS. 18 through 21, user interface presenter module 2054 may present by means of at least one user interface. In one embodiment, user interface presenter module 2054 may present to an individual by way of a touchscreen device. A user interface may include means by which an individual may interact with a system. Some examples of a user interface may include a touchscreen, a graphical user interface, a tactile interface, and/or a live user interface. In some instances, user interface presenter module 2054 may include a computer processor.

Further, operation 3106 illustrates presenting the indication to at least one mobile device. For example, as shown in FIGS. 18 through 21, mobile device presenter module 2056 may present to at least one mobile device. In one embodiment, mobile device presenter module 2056 may present to a mobile phone. A mobile device may include a portable computing device and may have wireless connection capability. Some examples of a mobile device may include a laptop or notebook computer, a personal digital assistant (PDA), an ipod, a smartphone, an Enterprise digital assistant (EDA), and/or a pager. In some instances, mobile device presenter module 2056 may include a computer processor.

FIG. 32 illustrates alternative embodiments of the example operational flow 2200 of FIG. 22. FIG. 32 illustrates example embodiments where operation 2220 may include at least one additional operation. Additional operations may include operation 3202, operation 3204, and/or operation 3206.

Operation 3202 illustrates presenting the indication to a third party. For example, as shown in FIGS. 18 through 21, third party presenter module 2058 may present to a third party. For example, third party presenter module 2058 may present to an individual's physician. A third party may include a party that is an independent party, person, and/or entity. Some examples of a third party may include a physician, a medical database, a hospital, a law enforcement agency, and/or a pharmacy. One example of reporting to a third party may include creating displays and reports for aggregating data from therapy results, further discussed in Bair et al., U.S. Pat. No. 6,067,523, which is incorporated herein by reference. In some instances, third party presenter module 2058 may include a computer processor and/or a communications device, such as a monitor and network link.

Further, operation 3204 illustrates presenting the indication to a health care provider. For example, as shown in FIGS. 18 through 21, health care provider presenter module 2060 may present to a health care provider. A health care provider may include a pharmacy, a pharmaceutical company, a medical device company, a research institution, a computer software and/or computer hardware company, a website, a nurse and/or a physician. In one embodiment, health care provider presenter module 2060 may present to a physician a prescribed combination artificial sensory experience and bioactive agent therapy via a secured website. In some instances, health care provider presenter module 2060 may include a computer processor.

Further, operation 3206 illustrates selectively presenting the indication only to the individual. For example, as shown in FIGS. 18 through 21, selective presenter module 2062 may selectively present only to the individual. Selective presenting may include limiting and/or blocking access of an individual's compliance results and/or a prescribed therapy, such as a prescribed artificial sensory experience and/or bioactive agent to a specific party. For example, selective presenter module 2062 may present only to individual 134 and may keep results of a certain combination therapy confidential from other entities. In one embodiment, an encryption key may be employed to protect selected information. In an additional example, selective presenter module 2062 may report only to a law enforcement agency and/or representative, such as a probation officer, and not to individual 134. In some instances, selective presenter module 3458 may include a computer processor.

FIG. 33 illustrates alternative embodiments of the example operational flow 2200 of FIG. 22. FIG. 33 illustrates example embodiments where operation 2220 may include at least one additional operation. Additional operations may include operation 3302.

Operation 3302 illustrates accepting a self report by an individual of compliance with a prescription for a virtual world configured to reduce breathing difficulty and presenting a prescribed dosage for an inhaler-dispensed bronchodilator at least partly based on the self report. For example, as shown in FIGS. 18 through 21, accepter module 2002 and presenter module 2032 may accept a self report by an individual of compliance with a prescription for a virtual world configured to reduce breathing difficulty and presenting a prescribed dosage for an inhaler-dispensed bronchodilator at least partly based on the self report. In some instances, accepter module 2002 may include a computer processor. In some instances, presenter module 2032 may include a computer processor, a computer printer, a mobile device, and/or a computer monitor.

Figure 34:
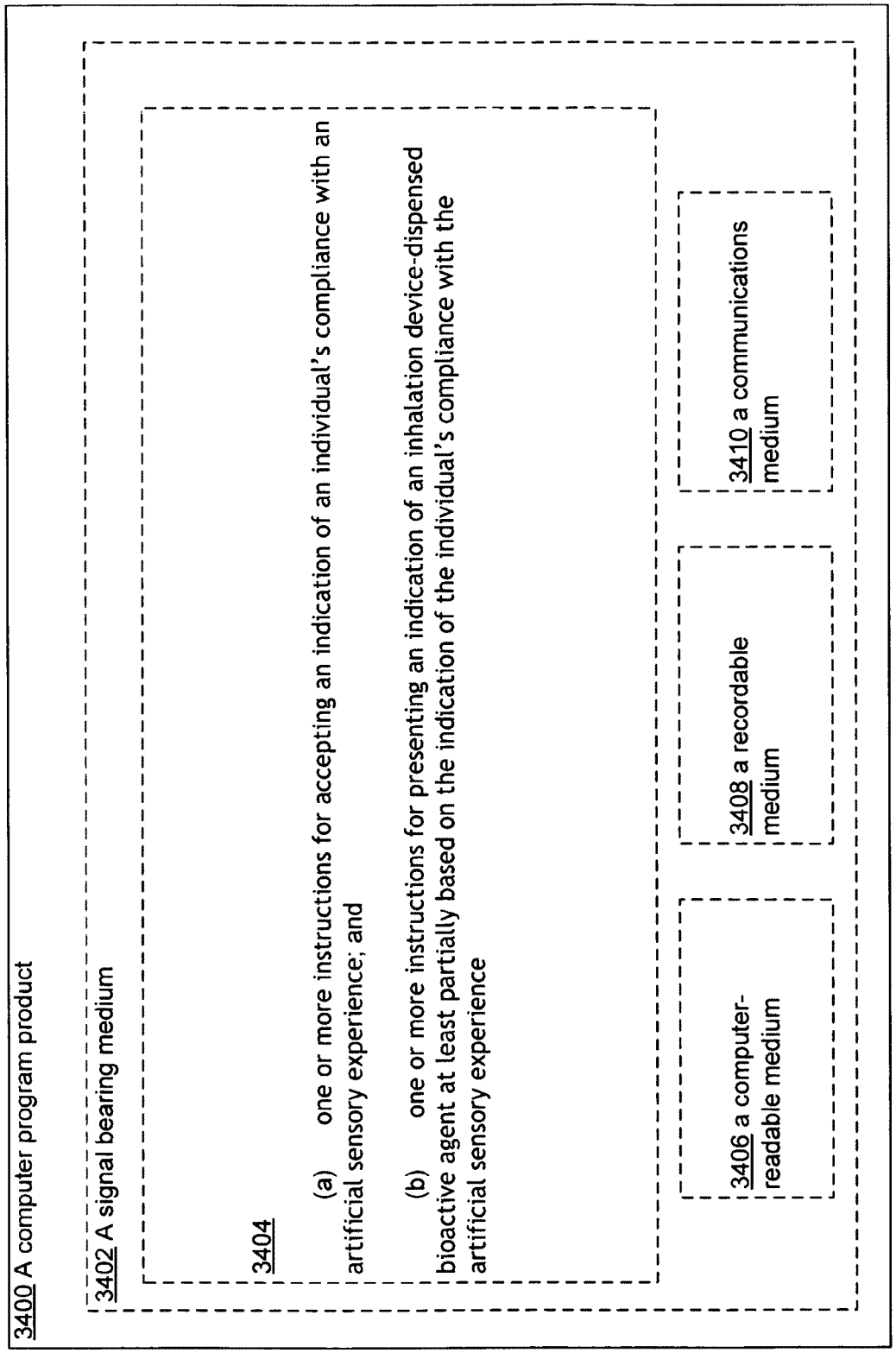
FIG. 34 illustrates a computer program product related to combining an inhaled bioactive agent and an artificial sensory experience.

FIG. 34 illustrates a partial view of an example computer program product 3400 that includes a computer program 3404 for executing a computer process on a computing device. An embodiment of the example computer program product 3400 is provided using a signal-bearing medium 3402, and may include one or more instructions for accepting an indication of an individual's compliance with an artificial sensory experience and one or more instructions for presenting an indication of an inhalation device-dispensed bioactive agent at least partially based on the indication of the individual's compliance with the artificial sensory experience. The one or more instructions may be, for example, computer executable and/or logic-implemented instructions. In one implementation, the signal-bearing medium 3402 may include a computer-readable medium 3406. In one implementation, the signal bearing medium 3402 may include a recordable medium 3408. In one implementation, the signal bearing medium 3402 may include a communications medium 3410.

Figure 35:
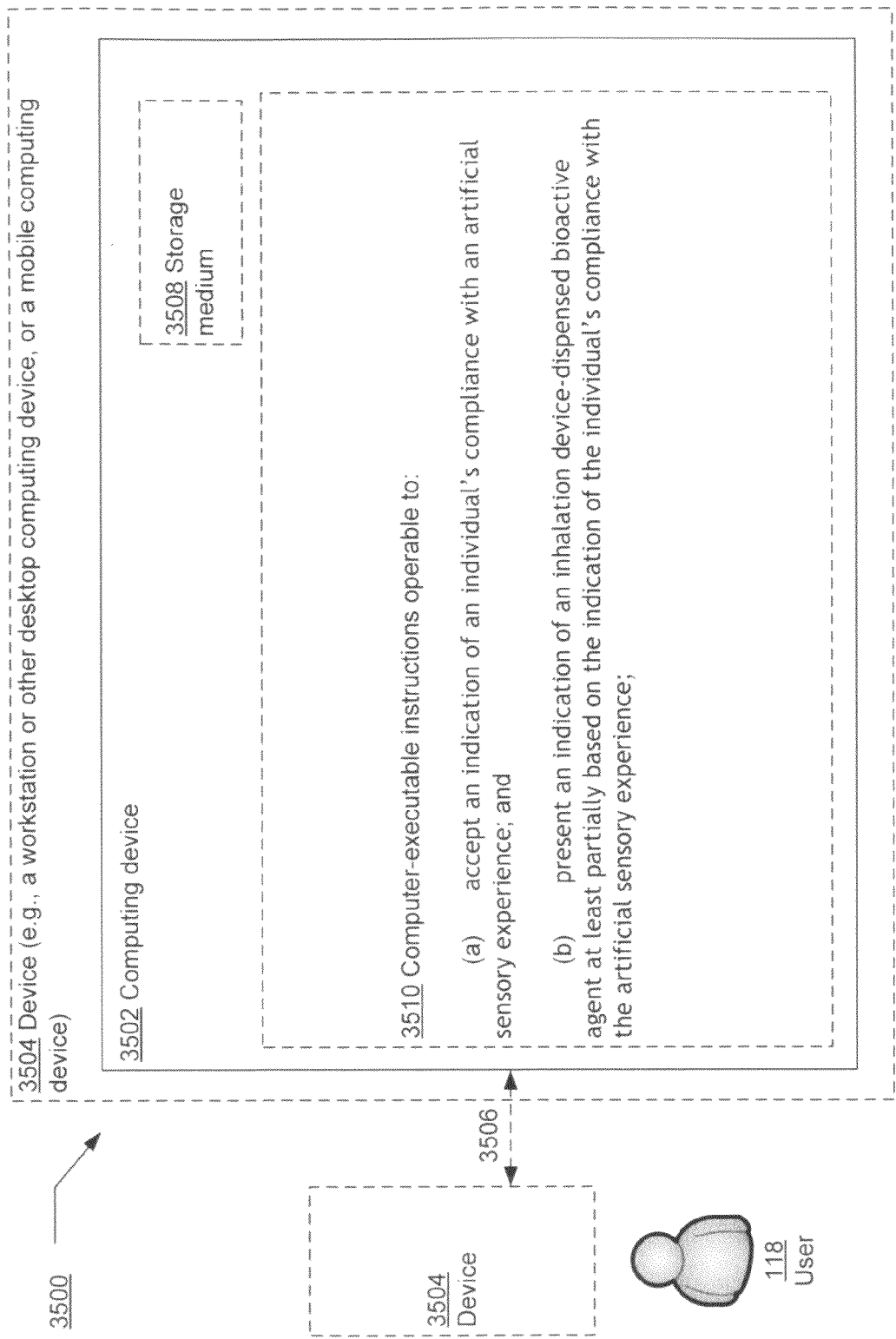
FIG. 35 illustrates a system related to combining an inhaled bioactive agent and an artificial sensory experience.

FIG. 35 illustrates an example system 3500 in which embodiments may be implemented. The system 3500 includes a computing system environment. The system 3500 also illustrates the user 118 using a device 3504, which is optionally shown as being in communication with a computing device 3502 by way of an optional coupling 3506. The optional coupling 3506 may represent a local, wide-area, or peer-to-peer network, or may represent a bus that is internal to a computing device (e.g., in example embodiments in which the computing device 3502 is contained in whole or in part within the device 3504). A storage medium 3508 may be any computer storage media.

The computing device 3502 includes computer-executable instructions 3510 that when executed on the computing device 3502 cause the computing device 3502 to accept an indication of an individual's compliance with an artificial sensory experience and present an indication of an inhalation device-dispensed bioactive agent at least partially based on the indication of the individual's compliance with the artificial sensory experience. As referenced above and as shown in FIG. 35, in some examples, the computing device 3502 may optionally be contained in whole or in part within the device 3504.

In FIG. 35, then, the system 3500 includes at least one computing device (e.g., 3502 and/or 3504). The computer-executable instructions 3510 may be executed on one or more of the at least one computing device. For example, the computing device 3502 may implement the computer-executable instructions 3510 and output a result to (and/or receive data from) the computing device 3504. Since the computing device 3502 may be wholly or partially contained within the computing device 3504, the device 3504 also may be said to execute some or all of the computer-executable instructions 3510, in order to be caused to perform or implement, for example, various ones of the techniques described herein, or other techniques.

The device 3504 may include, for example, a portable computing device, workstation, or desktop computing device. In another example embodiment, the computing device 3502 is operable to communicate with the device 3504 associated with the user 118 to receive information about the input from the user 118 for performing data access and data processing and presenting an output of the user-health test function at least partly based on the user data.

Although a user 118 is shown/described herein as a single illustrated figure, those skilled in the art will appreciate that a user 118 may be representative of a human user, a robotic user (e.g., computational entity), and/or substantially any combination thereof (e.g., a user may be assisted by one or more robotic agents). In addition, a user 118, as set forth herein, although shown as a single entity may in fact be composed of two or more entities. Those skilled in the art will appreciate that, in general, the same may be said of "sender" and/or other entity-oriented terms as such terms are used herein.

Following are a series of flowcharts depicting implementations. For ease of understanding, the flowcharts are organized such that the initial flowcharts present implementations via an example implementation and thereafter the following flowcharts present alternate implementations and/or expansions of the initial flowchart(s) as either sub-component operations or additional component operations building on one or more earlier-presented flowcharts. Those having skill in the art will appreciate that the style of presentation utilized herein (e.g., beginning with a presentation of a flowchart(s) presenting an example implementation and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory.

Further, implementation of at least part of a system for performing a method in one territory does not preclude use of the system in another territory.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Although user 118 is shown/described herein as a single illustrated figure, those skilled in the art will appreciate that user 118 may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system, comprising:
   means for accepting at least one indication related to at least one individual's compliance with at least one virtual world experience;
   means for determining at least one agent associated with at least one bioactive effect at least partially based on the means for accepting at least one indication related to at least one individual's compliance with at least one virtual world experience; and
   means for presenting at least one indication at least partially based on the means for determining at least one agent associated with at least one bioactive effect.

2. The system of claim 1, wherein the means for accepting at least one indication related to at least one individual's compliance with at least one virtual world experience comprises:
   means for accepting at least one report related to the at least one individual's compliance from at least one virtual world experience provider.

3. The system of claim 1, wherein the means for determining at least one agent associated with at least one bioactive effect at least partially based on the means for accepting at least one indication related to at least one individual's compliance with at least one virtual world experience comprises:
   means for utilizing at least one algorithm configured for comparing at least one effect of the at least one agent associated with at least one bioactive effect with at least one expected behavior of the at least one individual at one or more times substantially proximate to the at least one individual's use of the at least one virtual world experience.

4. The system of claim 1, wherein the means for presenting at least one indication at least partially based on the means for determining at least one agent associated with at least one bioactive effect comprises:
   means for selectively presenting the at least one indication only to the at least one individual.

5. A system, comprising:
   a computing device; and
   one or more instructions that when executed on the computing device cause the computing device to
      accept at least one indication related to at least one individual's compliance with at least one virtual world experience;
      determine at least one agent associated with at least one bioactive effect at least partially based on the at least one indication related to the at least one individual's compliance with the at least one virtual world experience; and
      present at least one indication at least partially based on the at least one agent associated with at least one bioactive effect.

6. The system of claim 5, wherein the computing device comprises:
   one or more of a personal digital assistant (PDA), a personal entertainment device, a mobile phone, a laptop computer, a tablet personal computer, a networked computer, a computing system comprised of a cluster of processors, a computing system comprised of a cluster of servers, a workstation computer, or a desktop computer.

7. The system of claim 5, wherein the computing device is operable to accept the at least one indication related to at least one individual's compliance with at least one virtual world experience, determine the at least one agent associated with at least one bioactive effect at least partially based on the at least one indication related to the at least one individual's compliance with the at least one virtual world experience, and present the at least one indication at least partially based on the at least one agent associated with at least one bioactive effect from at least one memory.

8. The system of claim 5, wherein, in causing the computing device to accept at least one indication related to at least one individual's compliance with at least one virtual world experience, the one or more instructions cause the computing device to:
   accept at least one indication related to at least one individual's compliance with at least one virtual world experience prescribed for the at least one individual.

9. The system of claim 5, wherein, in causing the computing device to determine at least one agent associated with at least one bioactive effect at least partially based on the at least one indication related to the at least one individual's compliance with the at least one virtual world experience, the one or more instructions cause the computing device to:
   determine a compatibility between the at least one virtual world experience and the at least one agent associated with at least one bioactive effect using at least one of at least one medical history, at least some experimental data, or at least one medical reference book.

10. The system of claim 5, wherein, in causing the computing device to present at least one indication at least partially based on the at least one agent associated with at least one bioactive effect, the one or more instructions cause the computing device to:
   present at least one identification of at least one prescribed inhalation device-dispensed bioactive agent.

11. A computer-implemented method, comprising:
   accepting at least one indication related to at least one individual's compliance with at least one virtual world experience;
   determining at least one agent associated with at least one bioactive effect at least partially based on the at least one indication related to the at least one individual's compliance with the at least one virtual world experience; and presenting at least one indication at least partially based on the at least one agent associated with at least one bioactive effect, wherein at least one of the accepting, determining, or presenting is at least partially implemented using computing hardware.

12. The computer-implemented method of claim 11, wherein accepting at least one indication related to at least one individual's compliance with at least one virtual world experience comprises:

accepting at least one report related to self compliance by the at least one individual.

13. The computer-implemented method of claim 11, wherein determining at least one agent associated with at least one bioactive effect at least partially based on the at least one indication related to the at least one individual's compliance with the at least one virtual world experience comprises:

utilizing at least one algorithm configured for matching at least one detected physiologic attribute of the at least one individual with at least one prescription inhalation device-dispensed medication at one or more times substantially proximate to the at least one individual's use of the at least one virtual world experience.

14. The computer-implemented method of claim 11, wherein presenting at least one indication at least partially based on the at least one agent associated with at least one bioactive effect comprises:

presenting at least one effect of the at least one agent associated with at least one bioactive effect in near real time.

15. A computer program product, comprising:

at least one non-transitory computer-readable medium including at least:

one or more instructions for accepting at least one indication related to at least one individual's compliance with at least one virtual world experience;

one or more instructions for determining at least one agent associated with at least one bioactive effect at least partially based on the one or more instructions for accepting at least one indication related to at least one individual's compliance with at least one virtual world experience; and one or more instructions for presenting at least one indication at least partially based on the one or more instructions for determining at least one agent associated with at least one bioactive effect.

16. The computer program product of claim 15, wherein the one or more instructions for accepting at least one indication related to at least one individual's compliance with at least one virtual world experience comprise:

one or more instructions for accepting at least one report related to the at least one individual's compliance from at least one health care provider.

17. The computer program product of claim 15, wherein the one or more instructions for determining at least one agent associated with at least one bioactive effect at least partially based on the one or more instructions for accepting at least one indication related to at least one individual's compliance with at least one virtual world experience comprise:

one or more instructions for indicating at least one of one or more recommended dosages or one or more recommended delivery methods.

18. The computer program product of claim 15, wherein the one or more instructions for presenting at least one indication at least partially based on the one or more instructions for determining at least one agent associated with at least one bioactive effect comprise:

one or more instructions for indicating at least one side effect of the at least one agent associated with at least one bioactive effect.

19. A system, comprising:

circuitry for accepting at least one indication related to at least one individual's compliance with at least one virtual world experience;

circuitry for determining at least one agent associated with at least one bioactive effect at least partially based on the circuitry for accepting at least one indication related to at least one individual's compliance with at least one virtual world experience; and circuitry for presenting at least one indication at least partially based on the circuitry for determining at least one agent associated with at least one bioactive effect.

20. The system of claim 19, wherein the circuitry for accepting at least one indication related to at least one individual's compliance with at least one virtual world experience comprises:

circuitry for accepting at least one indication related to usage of at least one virtual world experience by the at least one individual.

21. The system of claim 20, wherein the circuitry for accepting at least one indication related to usage of at least one virtual world experience by the at least one individual comprises:

circuitry for accepting at least one indication of computer usage.

22. The system of claim 21, wherein the circuitry for accepting at least one indication of computer usage comprises:

circuitry for accepting at least one indication of at least one of virtual world usage or a computer activity log.

23. The system of claim 20, wherein the circuitry for accepting at least one indication related to usage of at least one virtual world experience by the at least one individual comprises:

circuitry for accepting at least one indication of interactive device usage.

24. The system of claim 19, wherein the circuitry for accepting at least one indication related to at least one individual's compliance with at least one virtual world experience comprises:

circuitry for accepting at least one output from at least one of one or more presence detectors or one or more location reporting devices.

25. The system of claim 24, wherein the circuitry for accepting at least one output from at least one of one or more presence detectors or one or more location reporting devices comprises:

circuitry for accepting at least one output from at least one of one or more infrared detectors, one or more motion detectors, or one or more radio-frequency identification systems.

26. The system of claim 19, wherein the circuitry for accepting at least one indication related to at least one individual's compliance with at least one virtual world experience comprises:

circuitry for accepting at least one indication of one or more physiological measurements.

27. The system of claim 26, wherein the circuitry for accepting at least one indication of one or more physiological measurements comprises:

circuitry for accepting at least one indication of at least one of a respiratory rate, body weight, body mass index number, heart rate, blood oxygen level, or blood pressure proximate to administration of the bioactive agent.

28. The system of claim 26, wherein the circuitry for accepting at least one indication of one or more physiological measurements comprises:
circuitry for continuously monitoring at least one parameter of at least one physiological measurement.

29. The system of claim 26, wherein the circuitry for accepting at least one indication of one or more physiological measurements comprises:
circuitry for accepting at least one indication of at least one current parameter value compared with at least one expected parameter value.

30. The system of claim 19, wherein the circuitry for determining at least one agent associated with at least one bioactive effect at least partially based on the circuitry for accepting at least one indication related to at least one individual's compliance with at least one virtual world experience comprises:
circuitry for utilizing at least one algorithm configured for recommending the at least one agent associated with at least one bioactive effect.

31. The system of claim 30, wherein the circuitry for utilizing at least one algorithm configured for recommending the at least one agent associated with at least one bioactive effect comprises:
circuitry for utilizing at least one algorithm configured for identifying at least one contraindication of the at least one agent associated with at least one bioactive effect.

32. The system of claim 19, wherein the circuitry for presenting at least one indication at least partially based on the circuitry for determining at least one agent associated with at least one bioactive effect comprises:
circuitry for presenting the at least one indication to at least one output device.

33. The system of claim 32, wherein the circuitry for presenting the at least one indication to at least one output device comprises:
circuitry for presenting the at least one indication including at least via at least one user interface.

34. The system of claim 32, wherein the circuitry for presenting the at least one indication to at least one output device comprises:
circuitry for presenting the at least one indication to at least one mobile device.

35. The system of claim 19, wherein the circuitry for presenting at least one indication at least partially based on the circuitry for determining at least one agent associated with at least one bioactive effect comprises:
circuitry for presenting the at least one indication to at least one third party.

36. The system of claim 35, wherein the circuitry for presenting the at least one indication to at least one third party comprises:
circuitry for presenting the at least one indication to at least one health care provider.

37. The system of claim 19, wherein the circuitry for accepting at least one indication related to at least one individual's compliance with at least one virtual world experience, the circuitry for determining at least one agent associated with at least one bioactive effect at least partially based on the circuitry for accepting at least one indication related to at least one individual's compliance with at least one virtual world experience, and the circuitry for presenting at least one indication at least partially based on the circuitry for determining at least one agent associated with at least one bioactive effect comprise:
circuitry for accepting a self report by an individual of compliance with a prescription for a virtual world configured to reduce breathing difficulty and circuitry for presenting a prescribed dosage for an inhaler-dispensed bronchodilator at least partly based on the self report.

38. The system of claim 19, wherein the circuitry for accepting at least one indication related to at least one individual's compliance with at least one virtual world experience comprises:
circuitry for accepting an indication of an individual's compliance with an artificial sensory experience.

39. The system of claim 19, wherein the circuitry for determining at least one agent associated with at least one bioactive effect at least partially based on the circuitry for accepting at least one indication related to at least one individual's compliance with at least one virtual world experience and the circuitry for presenting at least one indication at least partially based on the circuitry for determining at least one agent associated with at least one bioactive effect comprise:
circuitry for presenting an indication of an inhalation device-dispensed bioactive agent at least partially based on the indication of the individual's compliance with the artificial sensory experience.

40. The system of claim 19, wherein the circuitry for determining at least one agent associated with at least one bioactive effect at least partially based on the circuitry for accepting at least one indication related to the at least one individual's compliance with the at least one virtual world experience comprises:
circuitry for determining at least one agent associated with at least one central nervous system effect at least partially based on the circuitry for accepting at least one indication related to the at least one individual's compliance with the at least one virtual world experience.

* * * * *